US008184295B2

(12) United States Patent
Myrick et al.

(10) Patent No.: US 8,184,295 B2
(45) Date of Patent: *May 22, 2012

(54) TABLET ANALYSIS AND MEASUREMENT SYSTEM

(75) Inventors: Michael L. Myrick, Irmo, SC (US);
Robert P. Freese, Pittsboro, NC (US);
John Blackburn, Charleston, SC (US);
David L. Perkins, Irmo, SC (US);
Leonard Zheleznyak, Pittsford, NY (US); Ryan Priore, Wexford, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/530,267

(22) PCT Filed: Mar. 27, 2008

(86) PCT No.: PCT/US2008/058393
§ 371 (c)(1),
(2), (4) Date: Sep. 14, 2010

(87) PCT Pub. No.: WO2008/121692
PCT Pub. Date: Oct. 9, 2008

(65) Prior Publication Data
US 2010/0328669 A1    Dec. 30, 2010

Related U.S. Application Data

(60) Provisional application No. 60/921,018, filed on Mar. 30, 2007.

(51) Int. Cl.
*G01N 21/00* (2006.01)
(52) U.S. Cl. ........................................ 356/436; 356/432
(58) Field of Classification Search .......... 356/432–442, 356/448, 39–42, 319, 326, 300, 337–343, 356/317–318, 301; 250/252.1, 576, 574, 250/461.2, 338.5, 200, 216, 573, 336.1
See application file for complete search history.

(56) References Cited

U.S. PATENT DOCUMENTS
3,632,435 A    1/1972    Eriksson et al.
(Continued)

FOREIGN PATENT DOCUMENTS
EP          0 600 334 A2    6/1996
(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

(Continued)

*Primary Examiner* — Tri T Ton
(74) *Attorney, Agent, or Firm* — Haynes and Boone, LLP

(57) ABSTRACT

The present subject matter relates to multivariate optical analysis systems employ multivariate optical elements and utilize multivariate optical computing methods to determine information about a product carried by light reflected from or transmitted through the product. An exemplary method of processing and monitoring the product includes introducing the product at an inspection point; illuminating the product with a spectral-specific light though an optic lens; directing the light that has passed through at least a section of the product through at least one multivariate optical element to produce a first signal, the directed light carrying information about the product; detecting the signal at a detector; and determining at least one property of the product based upon the detector output.

21 Claims, 10 Drawing Sheets

U.S. PATENT DOCUMENTS

| | | |
|---|---|---|
| 3,717,078 A | 2/1973 | Ogura |
| 3,761,724 A | 9/1973 | Dennis |
| 4,084,880 A | 4/1978 | Clow |
| 4,118,106 A | 10/1978 | Leith |
| 4,499,378 A | 2/1985 | Miyatake et al. |
| 4,595,832 A | 6/1986 | LaDelfe et al. |
| 4,607,914 A | 8/1986 | Fienup |
| 4,687,335 A | 8/1987 | Zupanick et al. |
| 4,687,337 A | 8/1987 | Stewart et al. |
| 4,704,536 A | 11/1987 | Sugiyama et al. |
| 4,821,338 A | 4/1989 | Naruse et al. |
| 4,891,574 A | 1/1990 | Nagaya et al. |
| 4,917,958 A | 4/1990 | Akai et al. |
| 4,934,782 A | 6/1990 | Soffer et al. |
| 4,968,148 A * | 11/1990 | Chow et al. .................. 356/427 |
| 4,981,332 A | 1/1991 | Smith |
| 5,005,946 A | 4/1991 | Brandstetter |
| 5,029,245 A | 7/1991 | Keranen et al. |
| 5,071,526 A | 12/1991 | Pletcher et al. |
| 5,090,807 A | 2/1992 | Tai |
| 5,103,340 A | 4/1992 | Dono et al. |
| 5,137,364 A | 8/1992 | McCarthy |
| 5,150,236 A | 9/1992 | Patel |
| 5,194,921 A | 3/1993 | Tambo et al. |
| 5,223,715 A | 6/1993 | Taylor |
| 5,259,381 A | 11/1993 | Cheung et al. |
| 5,289,289 A | 2/1994 | Nagaski |
| 5,321,539 A | 6/1994 | Hirbayashi et al. |
| 5,406,082 A | 4/1995 | Pearson et al. |
| 5,412,465 A | 5/1995 | Baylor et al. |
| 5,424,545 A | 6/1995 | Block et al. |
| 5,459,677 A | 10/1995 | Kowalski et al. |
| 5,479,164 A | 12/1995 | Yorks et al. |
| 5,504,332 A | 4/1996 | Richmond et al. |
| 5,513,022 A | 4/1996 | Son et al. |
| 5,555,128 A | 9/1996 | Khoury et al. |
| 5,622,868 A | 4/1997 | Clarke et al. |
| 5,641,962 A | 6/1997 | Perry et al. |
| 5,710,655 A | 1/1998 | Rumbaugh et al. |
| 5,717,605 A | 2/1998 | Komiya et al. |
| 5,734,098 A | 3/1998 | Kraus et al. |
| 5,737,076 A | 4/1998 | Glaus et al. |
| 5,747,806 A | 5/1998 | Khalil et al. |
| 5,750,994 A | 5/1998 | Schlager |
| 5,760,399 A | 6/1998 | Trygstad |
| 5,771,096 A | 6/1998 | Andersen |
| 5,781,289 A | 7/1998 | Sabsabi et al. |
| 5,799,231 A | 8/1998 | Gates et al. |
| 5,828,492 A | 10/1998 | Moser et al. |
| 5,831,742 A | 11/1998 | Watson et al. |
| 5,905,571 A | 5/1999 | Butler et al. |
| 5,939,717 A | 8/1999 | Mullins |
| 5,941,821 A | 8/1999 | Chou |
| 5,945,676 A | 8/1999 | Khalil et al. |
| 5,946,088 A | 8/1999 | Aldridge |
| 5,946,089 A | 8/1999 | Duer |
| 5,991,048 A | 11/1999 | Karlson et al. |
| 6,006,585 A | 12/1999 | Forster |
| 6,040,914 A | 3/2000 | Bortz et al. |
| 6,124,937 A | 9/2000 | Mittenzwey et al. |
| 6,137,108 A | 10/2000 | DeThomas et al. |
| 6,176,323 B1 | 1/2001 | Weirich et al. |
| 6,198,531 B1 | 3/2001 | Myrick et al. |
| 6,304,854 B1 | 10/2001 | Harris |
| 6,317,648 B1 | 11/2001 | Sleep et al. |
| 6,347,131 B1 | 2/2002 | Gusterson |
| 6,350,389 B1 | 2/2002 | Fujishima et al. |
| 6,420,708 B2 | 7/2002 | Wilks, Jr. et al. |
| 6,430,513 B1 | 8/2002 | Wang et al. |
| 6,437,326 B1 | 8/2002 | Yamate et al. |
| 6,469,785 B1 | 10/2002 | Duveneck et al. |
| 6,476,384 B1 | 11/2002 | Mullins et al. |
| 6,490,035 B1 | 12/2002 | Folestad et al. |
| 6,517,230 B1 | 2/2003 | Afnan et al. |
| 6,522,945 B2 | 2/2003 | Sleep et al. |
| 6,529,276 B1 | 3/2003 | Myrick |
| 6,573,999 B1 | 6/2003 | Yang |
| 6,600,560 B2 | 7/2003 | Mikkelsen et al. |
| 6,630,663 B2 | 10/2003 | Murphy et al. |
| 6,667,802 B2 | 12/2003 | Faus et al. |
| 6,690,464 B1 | 2/2004 | Lewis et al. |
| 6,697,195 B2 | 2/2004 | Weber et al. |
| 6,707,043 B2 | 3/2004 | Coates et al. |
| 6,711,503 B2 | 3/2004 | Haaland |
| 6,737,654 B2 | 5/2004 | Ducourant |
| 6,741,335 B2 | 5/2004 | Kinrot et al. |
| 6,748,334 B1 | 6/2004 | Perez et al. |
| 6,765,212 B2 | 7/2004 | Goetz et al. |
| 6,771,369 B2 | 8/2004 | Rzasa et al. |
| 6,776,517 B2 | 8/2004 | Afnan et al. |
| 6,798,518 B2 | 9/2004 | Difoggio et al. |
| 6,853,447 B2 | 2/2005 | Goetz |
| 6,870,629 B1 | 3/2005 | Vogel et al. |
| 6,952,267 B2 | 10/2005 | Rarac |
| 6,980,285 B1 | 12/2005 | Hansen |
| 6,982,431 B2 | 1/2006 | Modlin et al. |
| 6,995,840 B2 | 2/2006 | Hagler |
| 7,006,214 B2 | 2/2006 | Rzasa et al. |
| 7,123,844 B2 | 10/2006 | Myrick |
| 7,138,156 B1 | 11/2006 | Myrick et al. |
| 7,145,145 B2 | 12/2006 | Benson |
| 7,173,239 B2 | 2/2007 | DiFoggio |
| 7,245,374 B2 | 7/2007 | Hendriks |
| 7,271,883 B2 | 9/2007 | Newell et al. |
| 7,348,493 B2 | 3/2008 | Osanai et al. |
| 7,399,968 B2 | 7/2008 | Lewis et al. |
| 7,405,825 B2 | 7/2008 | Schuurmans et al. |
| 7,411,729 B2 | 8/2008 | Lyama et al. |
| 7,569,354 B2 | 8/2009 | Okano et al. |
| 7,623,233 B2 | 11/2009 | Freese et al. |
| 7,652,767 B2 | 1/2010 | Harsh et al. |
| 7,671,973 B2 | 3/2010 | Van Beek et al. |
| 7,697,141 B2 | 4/2010 | Jones et al. |
| 7,853,104 B2 | 12/2010 | Oota et al. |
| 7,889,346 B2 | 2/2011 | Myrick et al. |
| 7,911,605 B2 | 3/2011 | Myrick et al. |
| 7,920,258 B2 | 4/2011 | Myrick et al. |
| 7,993,276 B2 | 8/2011 | Nazarian et al. |
| 2001/0034064 A1 | 10/2001 | Turner et al. |
| 2002/0008215 A1 | 1/2002 | Evans |
| 2002/0050567 A1 | 5/2002 | Boudet et al. |
| 2002/0071118 A1 | 6/2002 | Shinbori et al. |
| 2002/0108892 A1 | 8/2002 | Goetz et al. |
| 2002/0109094 A1 | 8/2002 | Goetz et al. |
| 2002/0154315 A1 | 10/2002 | Myrick |
| 2003/0056581 A1 | 3/2003 | Turner et al. |
| 2003/0059820 A1 | 3/2003 | Vo-Dinh |
| 2003/0071988 A1 | 4/2003 | Smith et al. |
| 2003/0094495 A1 | 5/2003 | Knowles et al. |
| 2003/0111606 A1 | 6/2003 | Berghmans et al. |
| 2003/0117628 A1 | 6/2003 | Harju et al. |
| 2003/0202179 A1 | 10/2003 | Larsen et al. |
| 2004/0012782 A1 | 1/2004 | Mason et al. |
| 2004/0106098 A1 | 6/2004 | Chen et al. |
| 2004/0160601 A1 | 8/2004 | Womble et al. |
| 2004/0197850 A1 | 10/2004 | Baer et al. |
| 2004/0227086 A1 | 11/2004 | Haug et al. |
| 2005/0077476 A1 | 4/2005 | Poteet et al. |
| 2005/0087132 A1 | 4/2005 | Dickey et al. |
| 2005/0167264 A1 | 8/2005 | Sternbergh et al. |
| 2005/0251289 A1 | 11/2005 | Bonney et al. |
| 2005/0264815 A1 | 12/2005 | Wechsler et al. |
| 2005/0288906 A1 | 12/2005 | Drennen, III et al. |
| 2006/0035018 A1 | 2/2006 | Sakurai et al. |
| 2006/0051036 A1 | 3/2006 | Treado et al. |
| 2006/0093523 A1 | 5/2006 | Norman |
| 2006/0142955 A1 | 6/2006 | Jones et al. |
| 2006/0153492 A1 | 7/2006 | Treves et al. |
| 2006/0158734 A1 * | 7/2006 | Schuurmans et al. ........ 359/485 |
| 2006/0169902 A1 | 8/2006 | Watanabe |
| 2006/0197015 A1 | 9/2006 | Sterling et al. |
| 2006/0276697 A1 | 12/2006 | Demuth et al. |
| 2007/0035737 A1 | 2/2007 | Andrews et al. |
| 2007/0137292 A1 | 6/2007 | Xian et al. |
| 2007/0201136 A1 | 8/2007 | Myrick |
| 2007/0282647 A1 | 12/2007 | Freese et al. |
| 2007/0294094 A1 | 12/2007 | Alessandrini et al. |

| | | | |
|---|---|---|---|
| 2008/0111064 | A1 | 5/2008 | Andrews et al. |
| 2008/0231849 | A1 | 9/2008 | Myrick |
| 2008/0276687 | A1 | 11/2008 | Myrick et al. |
| 2008/0309930 | A1 | 12/2008 | Rensen |
| 2009/0002697 | A1 | 1/2009 | Freese et al. |
| 2009/0015819 | A1 | 1/2009 | Van Beek et al. |
| 2009/0033933 | A1 | 2/2009 | Myrick |
| 2009/0073433 | A1 | 3/2009 | Myrick et al. |
| 2009/0097024 | A1 | 4/2009 | Blackburn et al. |
| 2009/0140144 | A1 | 6/2009 | Myrick et al. |
| 2009/0216504 | A1 | 8/2009 | Priore et al. |
| 2009/0219538 | A1 | 9/2009 | Myrick et al. |
| 2009/0250613 | A1 | 10/2009 | Myrick et al. |
| 2009/0299946 | A1 | 12/2009 | Myrick et al. |
| 2009/0316150 | A1 | 12/2009 | Myrick et al. |
| 2010/0042348 | A1 | 2/2010 | Bakker |
| 2010/0073666 | A1 | 3/2010 | Perkins et al. |
| 2010/0141952 | A1 | 6/2010 | Myrick et al. |
| 2010/0149537 | A1 | 6/2010 | Myrick et al. |
| 2010/0153048 | A1 | 6/2010 | Myrick et al. |
| 2010/0182600 | A1 | 7/2010 | Freese et al. |
| 2010/0195105 | A1 | 8/2010 | Myrick et al. |
| 2010/0211329 | A1 | 8/2010 | Farquharson et al. |
| 2010/0245096 | A1 | 9/2010 | Jones et al. |
| 2010/0265509 | A1 | 10/2010 | Jones et al. |
| 2010/0302539 | A1 | 12/2010 | Myrick et al. |
| 2010/0305741 | A1 | 12/2010 | Myrick |
| 2010/0328669 | A1 | 12/2010 | Myrick et al. |

FOREIGN PATENT DOCUMENTS

| | | |
|---|---|---|
| EP | 1969326 A1 | 9/2008 |
| EP | 1974201 A1 | 10/2008 |
| EP | 2087328 A2 | 8/2009 |
| EP | 2140238 A1 | 1/2010 |
| JP | 57142546 A | 9/1982 |
| JP | 4001558 A | 1/1992 |
| JP | 07-053582 B2 | 6/1996 |
| JP | 11506206 | 6/1996 |
| JP | 9-3662 | 1/1997 |
| JP | 11506207 | 6/1999 |
| WO | 96/30746 | 10/1996 |
| WO | 2004/057284 A1 | 7/2004 |
| WO | 2005/062006 A1 | 7/2005 |
| WO | 2005/062986 A2 | 7/2005 |
| WO | 2006/031733 A2 | 3/2006 |
| WO | 2006/064446 A1 | 6/2006 |
| WO | 2006/137902 A2 | 12/2006 |
| WO | 2007/061435 A1 | 5/2007 |
| WO | 2007/061436 A1 | 5/2007 |
| WO | 2007/061437 A1 | 5/2007 |
| WO | 2007/062202 A1 | 5/2007 |
| WO | 2007/062224 A1 | 5/2007 |
| WO | 2007/064578 A2 | 6/2007 |
| WO | 2008/002903 A2 | 1/2008 |
| WO | 2008/057912 A2 | 5/2008 |
| WO | 2008/057913 A2 | 5/2008 |
| WO | 2008/121684 A1 | 10/2008 |

OTHER PUBLICATIONS

E.B. Martin et al., "Process Performance Monitoring Using Multivariate Statistical Process Control", IEE Proc.—Control Theory Appl., vol. 143, No. 2, pp. 132-144, Mar. 1996.

Mandelis et al., "Theory of Photopyroelectric Spectroscopy of Solids", Journal of Applied Physics, vol. 57, No. 9, pp. 4421-4430, 1985.

Zagonel et al., "Multivariate Monitoring of Soybean Oil Ethanolysis by FTIR", Talanta, vol. 63, No. 4, pp. 1021-1025, 2004.

Inon et al., "Combination of Mid- and Near-Infrared Spectroscopy for the Determination of the Quality Properties of Beers", Analytica Chimica Acta, vol. 571, No. 2, pp. 167-174, 2006.

Czarnik-Matusewicz et al., Temperature-Dependent Water Structural Transitions Examined by Near-IR and Mid-IR Spectra Analyzed by Multivariate Curve Resolution and Two-Dimensional Correlation Spectroscopy', Analytica Chimica Acta, vol. 544, No. 1-2, pp. 15-25, 2005.

Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.

Ghesti et al., "Application of Raman Spectroscopy to Monitor and Quantify Ethyl Esters in Soybean Oil Transesterification", Journal of the American Oil Chemists' Society, vol. 83, pp. 597-601, 2006.

Dereniak et al., *Infrared Detectors and Systems*, John Wiley & Sons: New York, Chapter 9, pp. 395-438, 1996.

Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.

Simcock et al, "Tuning D* with Modified Thermal Detectors", Applied Spectroscopy, vol. 60, No. 12, pp. 1469-1476, 2006.

Lang, "Ferroelectric Polymers and Ceramic-Polymer Composites", Key Engineering Materials, vol. 92-93, pp. 83-142, 1994.

Profeta et al., "Spectral Resolution in Multivariate Optical Computing", Spectrochimica Acta Part A: Molecular and Biomolecular Spectroscopy, vol. 67, pp. 483-502, 2007.

Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.

Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.

Knothe, "Analyzing Biodiesel: Standards and Other Methods", Journal of the American Oil Chemists Society, vol. 83, No. 10, pp. 823-833, 2006.

E.D. Palik, *Handbook of Optical Constants of Solids I*, Academic Press, San Diego, pp. 350-357, 1998.

M.L. Myrick, "Multivariate optical elements simplify spectroscopy", Laser Focus World 38, 91-94, 2002.

O. Soyemi et al., "Design and testing of a multivariate optical element: The first demonstration of multivariate optical computing for predictive spectroscopy", Anal. Chem. 73, No. 6, pp. 1069-1079, (2001).

M.L. Myrick et al., "A single-element all-optical approach to chemometric prediction", Vib. Spectrosc. 28, 73-81, 2002.

A.M.C. Prakash et al., "Optical regression: a method for improving quantitative precision of multivariate prediction with single channel spectrometers", Chemom. Intell. Lab. Syst. 46, 265-274, 1999.

R.A. Deverse et al., "Realization of the Hadamard multiplex advantage using a programmable optical mask in a dispersive flat-field near-infrared spectrometer", Appl. Spectrosc. 54, 1751-1758, 2000.

F.G. Haibach et al., "Precision in multivariate optical computing", Appl. Optics 43, 2130-2140, 2004.

M.L. Myrick et al., "Application of multivariate optical computing to simple near-infrared point measurements", Proceedings of the SPIE, Bellingham, VA, US, vol. 4574, pp. 208-215, 2002.

O.S. Heavens, *Optical Properties of Thin Solid Films*, Dover Publications, Inc., Mineola, USA, pp. 62-81, 242-249, 1991.

S. Betancourt et al., "Analyzing Hydrocarbons in the Borehole", Oilfield Review, pp. 54-61, Autumn 2003.

D. Eastwood et al., "Field applications of stand-off sensing using visible/NIR multivariate optical computing", Ground and Air Pollution Monitoring and Remediation, SPIE vol. 4199, pp. 105-114, 2001.

Haibach et al., "On-line Reoptimization of Filter Designs for Multivariate Optical Elements", Applied Optics, vol. 42, No. 10, pp. 1833-1838, Apr. 1, 2003.

Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.

M.P. Nelson et al., "Multivariate optical computation for predictive spectroscopy", SPIE Vo. 3261, pp. 232-243, 1998.

O. Soyemi et al., "A Simple Optical Computing Device for Chemical Analysis", Proceedings of SPIE Vo. 4284, pp. 17-28, 2001.

O. Soyemi et al., "Design of angle tolerant multivariate optical elements for chemical imaging", Applied Optics, vol. 41, No. 10, pp. 1936-1941, Apr. 1, 2002.

O. Soyemi et al., "Nonlinear Optimization Algorithm for Multivariate Optical Element Design", Applied Spectroscopy, vol. 56, No. 4, pp. 477-487, 2002.

O. Soyemi et al., "Novel Filter Design Algorithm for Multivariate Optical Computing", Advanced Environmental and Chemical Sensing Technology, Proceedings of SPIE Vo. 4205, pp. 288-299, 2001.

Strausz et al., "About the Colloidal Nature of Asphaltenes and the MW of Covalent Monomeric Units", American Chemical Society, Energy and Fuels 16, No. 4, pp. 809-822, 2002 (abstract).

N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.

N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.

Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.

Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.

M.P. Nelson et al., "Multivariate optical computation for predictive spectroscopy", Analytical Chemistry, vol. 70, No. 1, pp. 73-82, Jan. 1, 1998.

M.P. Nelson et al., "Fabrication and evaluation of a dimension-reduction fiberoptic system for chemical imaging applications", Review of Scientific Instruments, vol. 70, No. 6, pp. 2836-2843, Jun. 1999.

M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.

M. Groner et al., "Identification of Major Water-Soluble Fluorescent Components of Some Petrochemicals", Marine Pollution Bulletin, vol. 42, No. 10, pp. 935-941, 2001.

M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.

M.L. Myrick et al., "Spectral tolerance determination for multivariate optical element design", Fresenius J Anal Chem, 369:351-355, 2001.

R.J. Priore et al., "Miniature Stereo Spectral Imaging System for Multivariate Optical Computing", Applied Spectroscopy, vol. 58, No. 7, pp. 870-873, 2004.

M.L. Myrick et al., "Use of Molecular Symmetry to Describe Pauli Principle Effects on the Vibration-Rotation Spectroscopy of $CO_2(g)$", Journal of Chemical Education, vol, 81, No. 3, pp. 379-382, Mar. 2004.

M.N. Simcock et al., "Precision in imaging multivariate optical computing", Applied Optics, vol. 46., No. 7, pp. 1066-1080, Mar. 1, 2007.

Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.

P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.

Mullins et al., "Gas-Oil Ratio of Live Crude Oils Determined by Near-Infrared Spectroscopy", Applied Spectroscopy, vol. 55, No. 2, pp. 197-201, 2001.

Dobrowolski, J.A., et al., "Refinement of Optical Multilayer Systems With Different Optimization Procedures," Applied Optics, vol. 29, No. 9, Jul. 1, 1990, pp. 2876-2893.

Sullivan, Brian T., et al., "Implementation of a Numerical Needle Method for Thin-Film Design," Applied Optics, vol. 35, No. 28, Oct. 1996, pp. 5484-5492.

The Chemistry of Ferric Chloride; Printmaking Today, vol. 4, No. 2, 1995; Cello Press Ltd., Oxon, UK, 2 pages.

MSDS Hyper Glossary is a website http://www.ilpi.com/msds/ref/index.html, Safety Emporium Laboratory and Safety Supplies, retrieved on Feb. 10, 2012, 4 pages.

Handbook of Polymer Coating for Electronic Chemistry and Applications, 2nd ed., 1990.

Ryabenko, A.G., et al., "An Algorithm for Constructing the Basis of Optimal Linear Combinations . . . ", Pattern Recognition and Image Analysis, vol. 3, No. 1, 1993, 12 pages.

Moravskii, A.P., "Spectrophotometrtc Determination of the Yield of the C60 and C70 Fullerenes in Electric Arc Synthesis under Helium", Journal of Analytical Chemistry, vol. 53, No. 12, 1998, 8 pages.

MSDS No. F1080, Material Safety Data Sheet, Mallinckrodt Baker, Inc., Feb. 18, 2003, 6 pages.

Vasil'ev, G.K., et al., "Rotational and Vibrational Deactivation of Excited HF Molecules", Soy. Physics-JETP, vol. 41, No. 4, 1976, pp. 617-621.

Ryabenko, A.G., et al., "Numerical Study of a Pattern Recognition Multispectral System With Optimal Spectral Splitting," Pattern Recognition and Image Analysis, vol. 1, No. 3, 1991, 10 pages.

\* cited by examiner

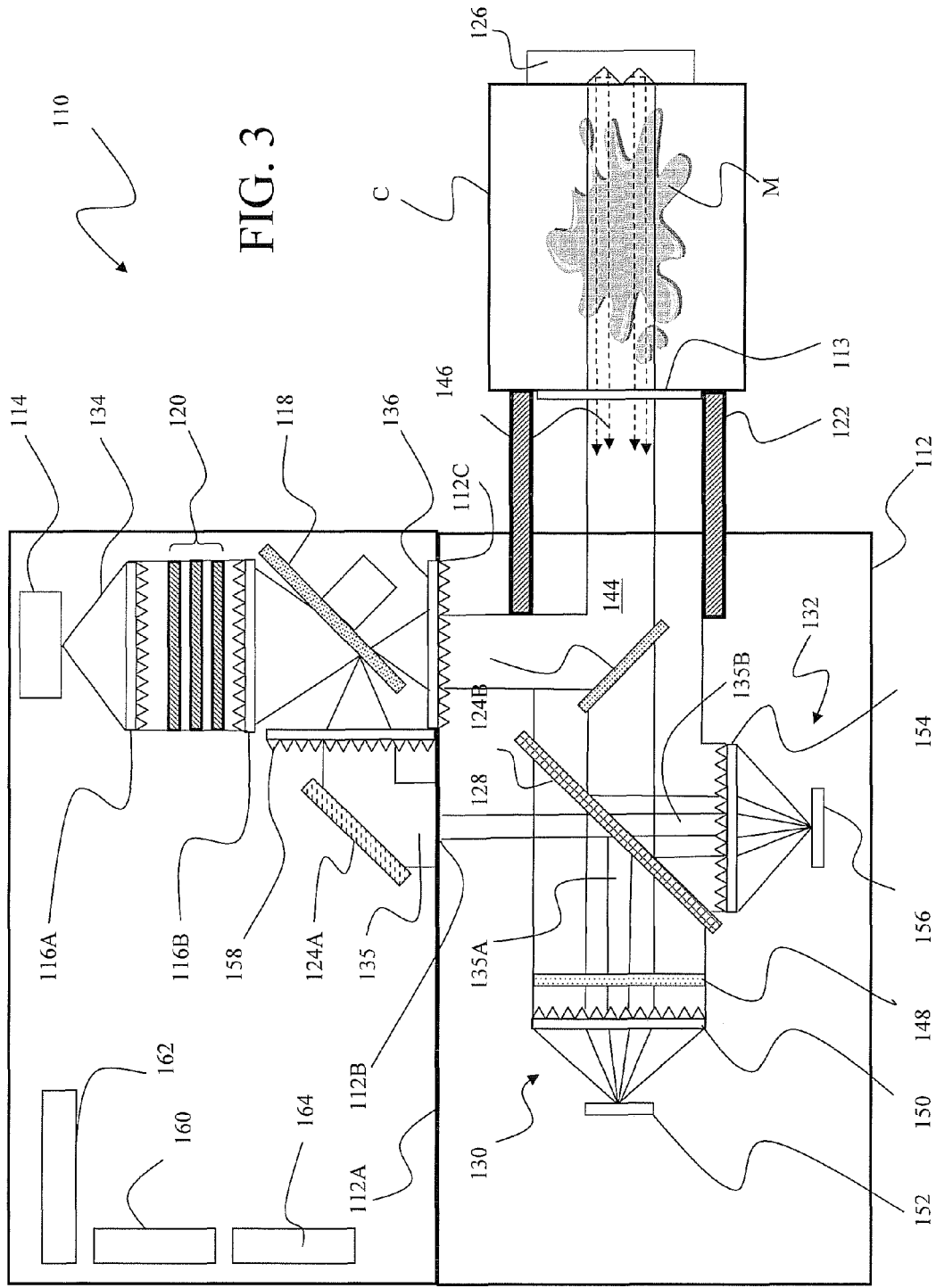

TABLET ANALYSIS AND MEASUREMENT SYSTEM

CROSS-REFERENCE TO RELATED APPLICATION

This application claims benefit of U.S. Provisional Patent Application, Ser. No. 60/921,018 filed Mar. 30, 2007.

FIELD OF THE INVENTION

The present subject matter relates to optical analysis systems using real-time multivariate optical computing. Multivariate optical computing (MOC) is a predictive spectroscopy technique that incorporates a multi-wavelength spectral weighting directly into analytical instrumentation. More particularly, the present subject matter relates to methodologies of using multivariate optical computing systems to illuminate a sample in which information about the sample can be analyzed from reflected or transmitted light in real time or near real time.

BACKGROUND OF THE DISCLOSURE

Light conveys information through data. When light interacts with matter, for example, it carries away information about the physical and chemical properties of the matter. A property of the light, such as its intensity, may be measured and interpreted to provide information about the matter with which the light interacted. That is, the data carried by the light through its intensity may be measured to derive information about the matter. Similarly, in optical communications systems, light data is manipulated to convey information over an optical transmission medium, for example, fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(Equation 1)}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{(Equation 2)}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \quad \text{(Equation 3)}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or coadds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

SUMMARY OF THE DISCLOSURE

Since multivariate optical element (MOE)-based MOC uses detectors that see all wavelengths emanating from an illumination source simultaneously—including wavelengths that carry no information—measurement noise is reduced and measurement precision is increased in a system of the present disclosure by making the system sensitive primarily to wavelengths carrying information. Additionally, the exemplary system controls a spectral range of the illumination source by using bandpass filters or spectral elements having predetermined transmission characteristics. Further, in some aspects of the present disclosure, the system shines a light signal directly onto a sample and eliminates the use of, for instance, a fiber optic probe; therefore, the component parts of the disclosure are simple and economical to manufacture, assemble and use, with improved signals when the attenuation typical of a fiber optic probe is removed. These and other aspects and advantages of the present disclosure will be apparent from the following description and the attached drawings, or can be learned through practice of the exemplary systems and methods according to the disclosure.

According to a particular embodiment of the present disclosure, an optical analysis system generally includes an illumination source for shining light or other radiative energy through a set of lenses. Light levels are maximized through the optical system to enhance transmission (reduce loss) of the light. The illumination source subsequently shines the light through a multi-window (e.g., 10-window) chopper wheel. The chopper wheel rotates, for instance, at 40 Hertz (Hz), which produces a light beam modulated at 400 Hz. A modulated light signal is beneficial for reliable performance of the photodetectors in the system.

Further in this aspect, the light beam may pass through one or more spectral elements or filters, which control the spectral region of the light that passes through the elements or filters (and onto a sample). The light may be reflected by a turning mirror down the center of the sampling tube and focused by a lens on the sample. The light is reflected back by the sample through the lens and back down the sampling tube, past the turning mirror. The light may pass through a beam splitter which reflects part of the light ("signal A") through an MOE and lens and onto a photodetector. Another part of the light ("signal B") may pass through a lens onto another photodetector and act as a reference signal. Thus, the system may measure signal A and signal B, and a ratio of the two signals may be used to measure a concentration of the sample, e.g., a chemical of interest. Additionally, monitoring of signal A and/or signal B independently, or in some combination, can provide other information, such as powder segregation, packing of materials, effect of particle size. More specifically, any algebraic combination of signals A and B can be used according to the disclosure; e.g., A and/or B independently; A divided by B; A plus B; A minus B; B divided by A; B minus A, etcetera. For example, a ratio of signal A to signal B can provide a chemical measurement; individually, A signal and/or B signal can provide other homogeneity measures including physical make-up of the sample, packing, particle size, and/or separate physical and chemical properties.

According to another aspect of the disclosure, a method of determining information carried by light may include providing an optical analysis system having a multivariate optical element disposed to receive a source light from an illumination source; filtering the source light through a spectral element in the optical element analysis system; reflecting the filtered light through an inner region of a cavity in a first direction of a sample to be measured, the cavity defining a second region disposed about the inner region; focusing the reflected light proximate the sample; reflecting the focused light from the sample through the second region in a second direction of a beamsplitter, the light being reflected from the sample carrying data from the sample; splitting the sample carrying light with the beamsplitter into a first light and a second light; optically filtering the data of the first light with the multivariate optical element into an orthogonal component; directing the first light filtered by the multivariate optical element onto a first photodetector; directing the second light onto a second photodetector; and comparing the orthogonal component to information present in the second light to determine a property of the sample. Also in this aspect, the light may be focused on, in or near the sample, the light having a focal point proximate the sample. Also in this aspect, the beamsplitter may be a 50/50 beamsplitter.

The method in this aspect may also include modulating the light from about 50 Hz to about 5000 Hz before filtering the light through the spectral element. Further, the method may include controlling a spectral range of the light source, and the spectral element may have a predetermined transmission characteristic for controlling the spectral range. Also in this aspect, the spectral element may be two or more spectral elements for controlling the spectral range of the light source.

The method may further include measuring a concentration of the sample ratio using a ratio of the first light and the second light. Additionally, the method may include monitoring the first light, the second light or combinations thereof to assess particle segregation of the sample; monitoring the first light, the second light or combinations thereof to assess density of the sample; monitoring the first light, the second light or combinations thereof to assess affect of particle size in the sample; monitoring the first light, the second light or combinations thereof to measure a chemical in the sample; monitoring the first light, the second light or combinations thereof to measure homogeneity of the sample and combinations of the foregoing steps.

Also in this aspect of the disclosure, the method may include using a fiber optic probe. Moreover, the method may include preparing a chemometric model to make a similar measurement of the light reflected from the sample as a measurement made by the optical analysis system. The method may also use the illumination light from the outer annular region with the filtered light through the inner region of the cavity to determine the property of the sample.

In yet another aspect of the disclosure, an optical analysis system may be configured in a transmission mode rather than a reflectance mode as in the foregoing embodiments. In the transmission mode, light would pass through a sample (e.g., a fluid sample) and be collected on a far side of the sample to enable, for instance, study of particle density in the fluid sample in conjunction with a chemical content. More particularly, the optical analysis system in this aspect may be configured to operate in the transmission mode in which the light is shone through the sample to a similar detection system. Additionally, or alternatively, a mirrored surface may be placed within the transmissive sample to reflect the light back into the detection system as described above.

In another aspect of the disclosure, an optical analysis system operating in a transmission configuration may be designed to improve a signal of interest. The light diversion path is designed to illuminate a sample, minimizing the amount of light going around the sample. This may be accomplished by focusing the light on the sample. By minimizing the light going around or past the sample, the associated noise in the signal is reduced. For a sample that is not round, a more elaborate lens or other focusing device may be utilized to produce a shaped beam to illuminate a larger portion of the sample than achievable from a round beam that does not exceed any dimension of the sample.

In another aspect of the disclosure, a method of determining information carried by light may include determining a plurality of orthogonal components of a first portion of a light signal, wherein each of the components has a predetermined shape with respect to a property of the first portion of the light signal that varies over a predetermined wavelength range; determining respective weightings for the orthogonal components so that the magnitude of the orthogonal components in the first portion of the light signal, weighted by the weightings, is proportional to the information present in the first portion in a predetermined relationship; providing an optical filter mechanism configured to optically filter the orthogonal components; disposing the optical filter mechanism to receive the first portion of the light signal; disposing a detector to receive a second portion of the light signal; detecting the property of the first portion of the light signal filtered by the optical filter mechanism; and analyzing the sample in real time by comparing the property of the first portion of the light signal to information in the second portion of the light signal.

In yet another aspect of the disclosure, an optical analysis system may include a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest of a liquid sample; a cavity in communication with the spectral element, the cavity being configured to direct the first light in a direction of the liquid sample; a conical mirror being configure to convert the first light reflecting from the liquid sample into a second light, the cavity being further configured to direct the second light; a beamsplitter being configured to split the second light into a first beam and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component to measure the data; and a second detector mechanism being configured to receive the second beam for comparison of the property of the orthogonal component to the second beam. The conical mirror in this aspect may include a coating of one of gold, aluminum or other element or material selected based on desired spectral region.

In another aspect of the disclosure, a method of high-speed processing and monitoring may include moving a product past an inspection point; illuminating at least a portion of the product with a light; directing light carrying information about the portion through at least one multivariate optical element to produce a first signal; detecting the first signal at a first detector; detecting a deflected portion of the light at a second detector; and determining at high speed at least one selected property of the portion as the portion moves past the inspection point based upon the detector outputs. The product in this aspect may be a pharmaceutical tablet, a pharmaceutical powder, a liquid, a gas, an emulsion, a solution, and a mixture.

In another aspect of the disclosure, a method of real-time processing and monitoring may include blending a material of interest with a secondary material; illuminating the blended materials with a light; reflecting light carrying information about the blended materials through at least one multivariate optical element to produce a first signal; detecting the first signal at a first detector detecting a deflected portion of the light at a second detector; and determining, in real time, at least one selected property of at least one of the blended materials as the material of interest and the secondary material are blended based upon respective detector outputs. In this aspect, real time may be defined as being faster than about 30 seconds, preferably faster than about 5 seconds, more preferably faster than about 1 second, still more preferably faster than about 1/10 of a second, yet more preferably faster than about 1/100 of a second, and most preferably faster than about 1/1000 of a second.

In a further aspect of the disclosure, a method of real-time pharmaceutical processing and monitoring may include blending a pharmaceutical powder by mixing an active agent with an excipient; illuminating the pharmaceutical powder with a spectral-specific light though an optic window, the optic window configured to focus the spectral-specific light into the pharmaceutical powder; reflecting light carrying information about the pharmaceutical powder through at least one multivariate optical element to produce a first signal; detecting the first signal at a first detector; detecting a deflected portion of the spectral-specific light at a second detector; and determining, in real time, at least one selected property of the pharmaceutical powder as the pharmaceutical powder is blended based upon respective detector outputs. In this aspect, the selected property of the pharmaceutical powder may be an active property of the active agent. Also in this aspect, the selected property may be a particulate size of the active agent. The selected property may also be a secondary property of the excipient. Furthermore, in this aspect of the disclosure a homogeneity asymptote of the pharmaceutical powder can be assessed.

In yet another aspect of the disclosure, a method of real-time pharmaceutical processing and monitoring is provided wherein real time may be defined as being between about 1/1000 of a second to about 30 seconds. The method may include illuminating a fluid in a container with a spectral-specific light though an optic window disposed proximate an aperture in a conduit in communication with the container; reflecting light carrying information about the fluid through at least one multivariate optical element to produce a first signal; detecting the first signal at a first detector; deflecting a portion of the spectral-specific light with a retroreflecting mirror; detecting the deflected portion at a second detector; and determining, in real time, at least one selected property of the fluid as the fluid flows past the optic window based on the detector outputs. The fluid in this aspect may be opaque in appearance. Moreover, the fluid may be a liquid chemical and the window may be configured to focus the spectral-specific light into the liquid chemical. The liquid chemical may also be a blend of at least one active pharmaceutical agent and at least one excipient. Alternatively, the fluid may be a gas, which may be clear or opaque.

In another aspect of the disclosure, a method of real-time processing and monitoring may include mixing a material of interest with a secondary material; illuminating the materials with a light; reflecting light carrying information about the materials through at least one multivariate optical element to produce a first signal; detecting the first signal at a first detector; detecting a deflected portion of the light at a second detector; and determining, in real time, at least one selected property of at least one of the materials based upon respective detector outputs. The selected property in this aspect may be determined based upon a compositional change. The compositional change may include a chemical reaction. Further, the compositional change may include a crystallization process.

In another aspect of the disclosure, a method of high-speed pharmaceutical processing and monitoring may include moving a plurality of portions of pharmaceutical product past an inspection point; illuminating at least one portion of the pharmaceutical product with a spectral-specific light though an optic window, the window configured to focus the spectral-specific light onto a portion at the inspection point; reflecting light carrying information about the portion through at least one multivariate optical element to produce a first signal; detecting the first signal at a first detector; detecting a deflected portion of the spectral-specific light at a second detector; and determining at high speed at least one selected property of the portion as the portion moves past the inspection point based upon the detector outputs. In this aspect, the portion may be a pharmaceutical tablet or a quantity of pharmaceutical powder. The portion may be a chemical sample in a closed container, and the container may be at least partially transparent to light focused onto the chemical sample. According to this aspect of the disclosure, the portion may be moved past the inspection point in at least one minute, preferably in at least 10 seconds. Still more preferably, at least 10 portions per second may be moved past the inspection point.

In a further aspect of the disclosure, a method of processing and monitoring a solid phase may include moving a solid product past an inspection point; illuminating the solid product with a spectral-specific light though an optic lens; reflecting light from the solid product through at least one multivariate optical element to produce a first signal, the reflected light carrying information about the solid product; detecting the first signal at a first detector; deflecting a portion of the reflected light in a direction of a second detector, the second detector configured to detect the deflected portion; and computing at high speed at least one selected property of the solid product as the solid product moves past the inspection point based upon the detector outputs. In this aspect, the solid product may be a pharmaceutical tablet or a quantity of pharmaceutical powder. Also in this aspect of the disclosure, the solid product may be a powder mixture in a closed container, and the container may be at least partially transparent to light focused onto the powder mixture.

In another aspect of the disclosure, an optical analysis system may include a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest of a sample, e.g., a liquid, the first light being directed into the sample; a conical mirror being configured to convert the first light from the sample into a second light; a beam splitter being configured to split the second light into a first beam and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component to measure the data; and a second detector mechanism being configured to receive the second beam for comparison of the property of the orthogonal component to the second beam. The conical mirror may include a coating of gold or aluminum, and may be a collimating mirror configured to diffuse the first light into the second light.

In this aspect of the disclosure, the optical analysis system may further include a cavity in communication with the spectral element, the cavity being configured to direct the first light in a direction of the sample. The cavity may be specular and configured to direct the second light to avoid attenuation.

According to yet another aspect of the disclosure, an optical analysis system may include a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest of a sample; a light diversion path for diverting the first light into the sample, the first light being transmitted through the sample and emerging as a second light; a beam splitter being configured to split the second light into a first beam:and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component to measure the data; and a second detector mechanism being configured to receive the second beam for comparison of the property of the orthogonal component to the second beam. The light diversion path, for example, may be a fiber-optic cable or a plurality of mirrors arranging a linear or tortuous light path.

In another aspect of the disclosure, a method of high-speed processing and monitoring may include moving a product past an inspection point; illuminating at least a section of the product with a light; directing the light that has passed through the section and is carrying information about the product through at least one multivariate optical element to produce a first signal; deflecting a portion of the light to produce a second signal; detecting the first signal at a first detector; detecting the second signal at a second detector; and determining at least one property of the product based upon the detector outputs as the product moves past the inspection point at a rate of about one section per second to about five sections per second. The product may be a solid product, a liquid product or a gas product. The solid product may be a pharmaceutical tablet or a pharmaceutical powder. Moreover, the product may be an emulsion, a solution, or a mixture.

Also in this aspect, an illumination source for the light may be disposed or positioned proximate the section of the product and the light that has passed through the section may be reflected from the section in a direction of the detectors. Alternatively, or additionally, the illumination source may be disposed proximate the product and the light that has passed through the section may transmit through the product in a direction of the detectors.

The method may further include diverting a part of the light from the illumination source into the product along a light diversion path. The light diversion path may be a fiber-optic cable or a series of mirrors. The method may also include diffusing the light that has passed through the section before the light is directed to the multivariate optical element. The light may be diffused by a collimating mirror.

In an additional aspect of the disclosure, a method of processing and monitoring a product may include introducing a product at an inspection point; illuminating the product with a spectral-specific light though an optic lens; directing the light that has passed through at least a section of the product through at least one multivariate optical element to produce a first signal, the directed light carrying information about the product; detecting the first signal at a first detector; deflecting a portion of the directed light to produce a second signal in a direction of a second detector, the second detector configured to detect the second signal; and determining at least one property of the product at a rate of about one section of the product per second to about five sections of the product per second based upon the detector outputs. The product may be a solid, liquid or gas and be disposed in a closed container. The container may be at least partially transparent to light focused onto the product. The product may be moved past the inspection point and/or the optic lens may be moved past the product.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof to those of ordinary skill in the art, is set forth more particularly in the remainder of the specification, including reference to the accompanying figures, in which:

FIG. 3 is schematic plan view of another embodiment of a real time measurement system constructed in accordance with the present subject matter particularly showing a retroreflecting mirror for use with clear;

Figure 1:
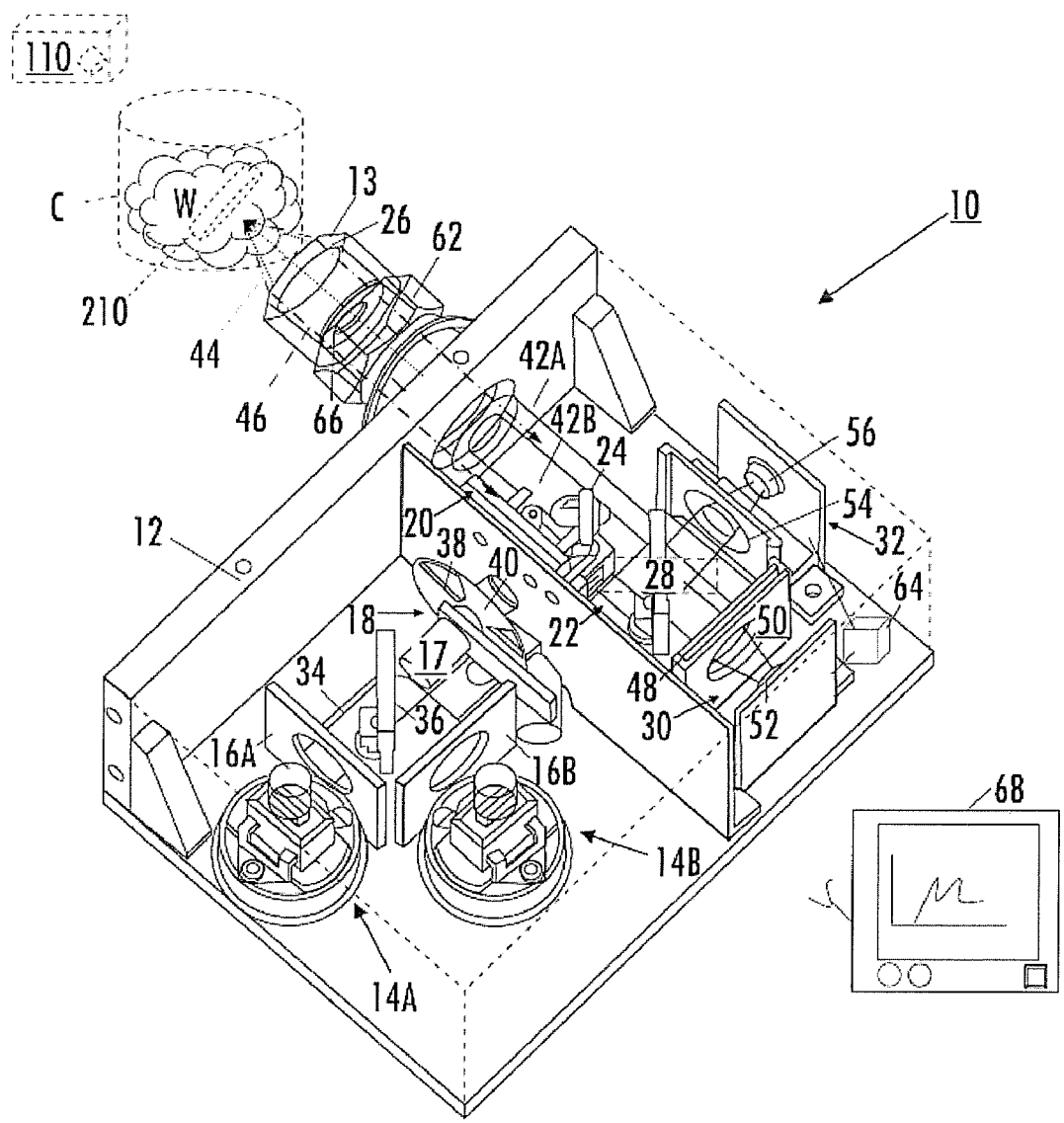
FIG. 1 is a top perspective view of an exemplary embodiment of a real time measurement system constructed in accordance with the present subject matter.

Repeat use of reference characters throughout the present specification and appended drawings is intended to represent same or analogous features or elements of the present subject matter.

DETAILED DESCRIPTION OF THE DISCLOSURE

Detailed reference will now be made to the drawings in which examples embodying aspects of the present disclosure are shown. As used herein, the term "light" is broadly used to mean any form of radiation or radiative energy including, for instance, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; penetration, however slight, into a sample such as a particulate sample or opaque fluid sample; or passage through a sample such as a fluid sample.

As used herein, a sample W (alternatively, workpiece or material M) can mean an analyte undergoing analysis over a range of conditions. The sample W can be a solid or a fluid including but not limited to a powder, a pharmaceutical powder mixed with lactose and other excipient materials, a chemical, a polymer, a petroleum product, a solution, a dispersion, an emulsion and combinations of these solids and fluids.

Multivariate optical computing (MOC) is generally described in U.S. Pat. No. 6,198,531 B1 to Myrick et al. and in U.S. Pat. No. 6,529,276 B1 to Myrick, both of which are incorporated herein in full for all purposes by reference thereto.

Figure 2:
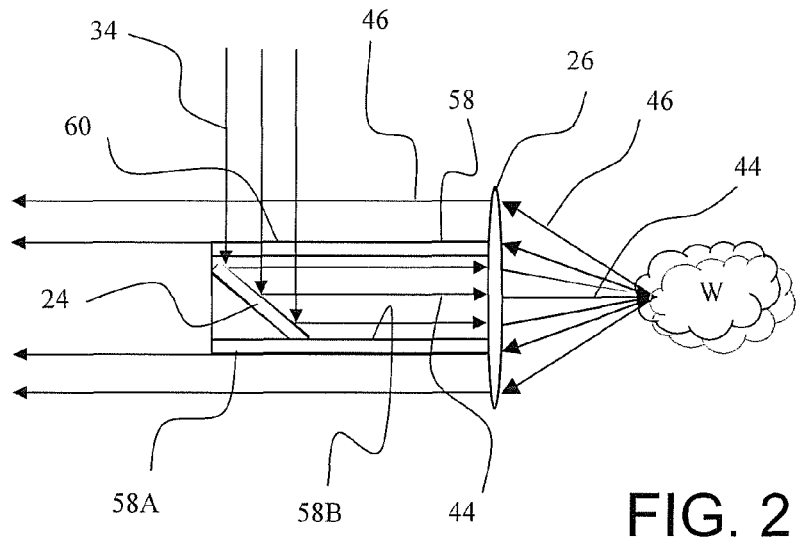
FIG. 2 is a schematic view of a concentric cavity as in FIG. 1 in accordance with a further embodiment of the present subject matter.

As generally shown in FIGS. 1 and 2, an optical analysis system according to an aspect of the disclosure is designated by the element number 10. The system 10 is designed around at least one application specific multivariate optical element (MOE) based on spectra typically provided by an end-user. The system design takes into account representative spectra of compounds of interest, basic and expected concentrations of interest across a range of expected interferents. Also, the system 10 incorporates the desired spectral regions (UV, VIS, NIR, MIR, IR) of interest.

In the embodiment shown in FIG. 1, the optical analysis system 10 broadly includes a housing 12, a plurality of illumination or light sources 14A, 14B, a concentric light tube or cavity 22, a focusing lens 26, at least one beam splitter 28, a first detector 30 including a multivariate optical element 48 and a second detector 32. Although FIG. 1 shows a generally square or rectangle shaped, metallic housing 12 and two detectors 30, 32 arranged therein, those of ordinary skill in the art will appreciate that a variety of shapes, dimensions, component placements and material makeup of the components can be substituted for the examples shown according to various requirements such as government regulations, customer specifications and the like. Moreover, as discussed below with respect to an embodiment of the disclosure, the sample W can be analyzed using a PCR-type model without a/or beamsplitter 28 in an off-line approach.

Those of ordinary skill in the art will also understand that although system 10 can be a measurement system operating in reflectance mode, system 10 can also be configured to operate in a transmission mode in which light is shone through the sample W from an incident side of the sample W to a similar detection system 110 on another side of the sample W. Alternatively, or additionally, a mirrored surface 210 can be placed within the transmissive sample W to reflect the light back into the detection system 10. Therefore, the disclosure is not limited only to the examples shown in the figures.

With more particular reference to FIG. 1, housing 12 (shown partially in phantom for clarity) can be metal such as stainless steel, a plastic material such as high-density polyethylene (HDPE) or any durable material for protecting the components of optical analysis system 10. As shown, sampling of sample W is accomplished through window 13 in enclosed optical analysis system 10. Accordingly, enclosed optical analysis system 10 can be used in a dangerous (e.g., explosive) environment. As will be described in detail below, window 13 is transmissive in a known manner in a spectral region of interest.

As briefly introduced above, illumination sources 14A, 14B are chosen to provide source light 34, which has a spectral range determined by a spectral range of interest for the intended sample measurement. Illumination sources 14A, 14B are also chosen based on reliability, intensity, temperature generation, and other factors. Illumination sources 14A, 14B are also redundant to further enhance reliability. As shown in FIG. 1, redundant illumination sources 14A, 14B can be oriented at 90 degrees from each other with a "50-50" beamsplitter 36 located near their center point to provide a constant source of illumination.

FIG. 1 further shows a plurality of lenses 16A, 16B, respectively associated with each of the illumination sources 14A, 14B. Lenses 16A, 16B are used to collect the light signal 34 from illumination sources 14A, 14B and to focus the light signal 34 on a modulator or chopper wheel 18, described below. As shown, lenses 16A, 16B are positioned to capture as much of the light signal 34 as possible from illumination sources 14A, 14B. Additionally, chopper-focusing lens 17 is used to focus as much of the light signal 34 as possible through the chopper wheel 18. Those of ordinary skill in the art will recognize that lenses 16A, 16B, 17 are selected for focal length, position, material of construction and the like to enhance transmission (reduce loss) of the light signal 34. For example, in the design of the optical path, if the illumination sources 14A, 14B is a lamp, slight magnification or demagnification of the source is generally obtained at the sample W, depending on the ratios of the focal length, e.g., of lens 16A to that placed after illumination source 14A to collimate it. Ultimately, the image of illumination source 14A on the sample W is directed toward detectors 30, 32 as described below and again with some slight magnification or demagnification, depending on the ratios of the focal length, e.g., of lenses 16A to that of, e.g., lens 50 placed before the detector 30 to focus reflected light 46 onto detector 30. Thus, it should be understood that there is a relationship between the focal lengths of lenses 16A, 16B that must be maintained in order to make sure the ultimate image of the source-excited region of the sample W that is formed on detectors 30, 32 is suited to the physical dimensions of detectors 30, 32.

Those of ordinary skill in the art will further appreciate that lenses 16A, 16B shown for example in FIG. 1 are plastic, Fresnel lenses well suited for use in an infrared (IR) region of about 1000 nanometers (nm) to about 3000 nm. However, those of ordinary skill in the art will understand that lenses 16A, 16B are not limited to only plastic, Fresnel lenses and that other types of lenses and materials such as glass can be used for these lenses.

As further shown in FIG. 1, chopper wheel 18 includes a plurality of alternating windows 38 and a plurality of alternating spokes 40 that modulate the light signal 34 from about 50 Hertz (Hz) to about 5000 Hz to enable a plurality of photodetectors 52, 56 in the optical system 10 to perform properly, as will be further described below. As shown in this example, chopper wheel 18 is a 10-window chopper wheel rotating at 40 Hz which provides a chopped signal of 400 Hz. The number and arrangement of the windows 38 and spokes 40, and thus the chopper frequency, are chosen based on several variables, including a rate of motion of the sample material W moving past the sampling window 13; a performance characteristic of the photodetectors 52, 56 and amplification system; a predetermined sampling rate of the data collection and analysis system 10; physical properties of a chopper motor (not shown), control system (not shown), and the chopper wheel 18 (including material(s) of the windows 38).

More particularly, the number of windows 38 in the chopper wheel 18 can be adjusted to provide a suitable degree of signal modulation. In one aspect of the present disclosure, chopper wheel 18 has open windows 38 and black spokes 40, which block the light signal 34. In another aspect, different materials can be placed in the windows 38 to provide different spectral characteristics for the various windows 38. Moreover, the transmission characteristic of these windows 38 could be used as further spectral elements. Windows 38 can also contain multivariate optical elements (MOE) such as those described below with respect to a MOE 48 of the MOE detector 30.

FIG. 1 also illustrates a plurality of bandpass filters or spectral elements 20 located in a path of the light signal 34 after the light signal 34 has passed through chopper wheel 18. As briefly discussed above, spectral elements 20 are selected based on a desired application; i.e., to analyze a particular sample W. Spectral elements 20 are chosen so that the spectral region of illumination covers the desired range; i.e., related to a particular chemical material of interest. For example, if 1500-2000 nanometers (nm) of light wavelengths is the desired spectral region, the spectral elements 20 are selected to filter out wavelengths are not in that region. An example of these spectral elements is a SCHOTT brand filter, which can be a long pass, short pass, or band pass filter. By way of further example but not of limitation, some suitable materials for use as the spectral elements 20 are listed in the following table.

TABLE 1

Properties of Select Transmitting Materials

| Material | Comments | SWL cm−1 | LWL cm−1 | RI | Solubility g/100 g | Hardness Kg/mm 2 | MP °C. | pH Range |
|---|---|---|---|---|---|---|---|---|
| AMTIR | SeAsGe glass | 11000 | 593 | 2.5 | 0 | 170 | 370 | 1-9 |
| BaF 2 | Barium Fluoride | 66600 | 691 | 1.45 | 0.17 | 82 | 1280 | 5-8 |
| Ca F 2 | Calcium Fluoride | 79500 | 896 | 1.4 | 0.0017 | 158 | 1360 | 5-8 |
| CsI | Cesium Iodide, very hygroscopic | 42000 | 172 | 1.73 | 44 | 20 | 621 | NA |
| Diamond | Type IIa, strong IR absorbance between 2700-1800 cm−1 | 30000 | <2 | 2.4 | 0 | 5700 | 550 fp | 1-14 |
| Ge | Germanium, becomes opaque at elevated temperatures | 5500 | 432 | 4 | 0 | 780 | 936 | 1-14 |
| KBr | Potassium Bromide | 48800 | 345 | 1.52 | 53 | 6 | 730 | NA |
| KCl | Potassium Chloride | 55600 | 385 | 1.45 | 35 | 7 | 776 | NA |
| KRS-5 | Thallium Bromide/ Thallium Iodide | 17900 | 204 | 2.37 | 0.05 | 40 | 414 | 5-8 |
| NaCl | Sodium Chloride | 52600 | 457 | 1.49 | 36 | 18 | 801 | NA |
| Polyethylene | For Far-IR, swells with some organic solvents | 625 | <4 | 1.52 | 0 | | 110 | 1.5-14 |
| SiO 2 | Silicon Dioxide | 50000 | 2315 | 1.53 | 0 | 460 | 1713 | 1-14 |
| Si | Silicon, strong IR absorbance between 624-590 cm−1 | 8900 | 624.30 | 3.41 | 0 | 1150 | 1420 | 1-12 |
| ZnS | Zinc Sulfide | 17000 | 690 | 2.2 | 0 | 240 | 1830 | 5-9 |
| ZnSe | Zinc Selenide | 15000 | 461 | 2.4 | 0 | 120 | 1526 | 5-9 |

Note:
To convert from wavenumber (cm−1) to wavelength (μm), divide 10,000 by the wavenumber; e.g., 5500 cm−1 is equivalent to 1.8 μm or 1800 nm.
SWL—Shortest wavelength for transmission, 1 mm, 50% transmission
LWL—Longest wavelength for transmission, 1 mm, 50% transmission
RI—Refractive Index, at relevant wavelength
MP—Melting point With reference now to FIGS. 1 and 2, light signal 34 exits spectral elements 20 and reflects off a first mirror or turning mirror 24. It will be appreciated that although the turning mirror 24 is shown at an angle of about 45 degrees with the light signal 34 reflecting at this angle, the turning mirror 24 can be turned to any desired angle. As known to those of ordinary skill in the art, turning mirror 24 can be a powered turning mirror powered by a battery, by electricity or the like. Further description of power sources and implementation with turning mirror 24 is not necessary for one of ordinary skill in the art understand this aspect of the disclosure. Those of ordinary skill in the art will further appreciate that although the turning mirror 24 is shown as a unitary mirror, devices constructed in accordance with the present disclosure can utilize multiple mirrors arranged in or adjustable to a variety of positions.

As further shown in FIGS. 1 and 2, the filtered and reflected light signal 34 becomes a reflected light 44 after being reflected by the turning mirror 24. The reflected light 44 thus continues down the concentric sampling tube 22, briefly introduced above, in a direction of the sample W. As shown and further described below, the concentric tube 22 includes an inner annular region (also referred to as tube or chamber) 42A and an outer annular region 42B (also, tube or chamber). In this example, the reflected light 44 is reflected along the inner annular region 42A. It will be understood that the illumination sources 14A, 14B and the detectors 30, 32 are shown in an exemplary orientation and can be reversed. It will be further appreciated that the light signal 34 and the reflected light 44 are shown collimated for simplicity. However, the light signal 34 and the reflected light 44 may not be completely collimated because the illumination sources 14A, 14B can be extended rather than point sources.

The focusing lens 26 in FIGS. 1 and 2 is located near an end of the tube 22 proximate the sample W. As shown in this example, the end of the tube 22 is sealed with the transmissive window 13. The transmissive window 13 should be uniformly transmissive across wavelengths, but if it is not, the transmission characteristics of the transmissive window 13 are taken into account for the design of the system 10 and in particular the MOE 48. This embodiment may include an additional focusing lens 66, which can be solid or have one or more apertures as shown in FIG. 1. The additional focusing lens 66 is used to focus or collimate a carrier light 46, described below, in a direction of the tube 22.

As further shown in FIGS. 1 and 2, the focusing lens 26 focuses the reflected light 44 onto, into or near the sample W via the transmissive window 13. In this example, the reflected light 44 is focused with a focal point 0-5 mm into the sample W. In addition to isolating components of the optical analysis system 10 from an external environment, the transmissive window 13 further enables a mixing vessel or container C, which is being tested/sampled into, to remain intact. As shown in this example, a one-inch (inner diameter) Swagelok® brand connector 62, available from Swagelok Corporation, Solon, Ohio, is used to connect the optical analysis system 10 to the mixing vessel C. This arrangement permits the reflected light 44 to be sent down the tube 22 (inner region 42A), interact with the material of interest W, reflect back up the tube 22 (outer region 42B), and be directed to the detectors 30, 32 as further described below.

As most clearly shown in FIG. 2, a tube 58 defines an aperture 60 for passage of the light signal 34 in a direction of the turning mirror 24. Separation of the illumination and reflection light paths or signals 44, 46 can be further defined or separated by physically separating the inner and outer regions 42A, 42B employing the tube 58. Any minimal reduction in light return of the carrier light 46 described below (caused by physical occupation of a portion of the outer region 42B by the tube 58) is offset by improvement in the amount of backscattered radiation returned to the detectors 30, 32 without encountering the sample W.

More specifically, the tube 58 is used to reduce a non-zero background measurement. The non-zero background measurement can occur in an optical system when a small amount of scattered light is returned to a detector even when no sample is present. Some of the scattered light can be reflected from a window, and some can come from the lenses themselves.

FIG. 2 shows that tube 58 is placed around the mirror 24 before the lens 26. Tube 58 reduces background signals by separating the excitation and collection light paths 34, 46 to minimize "cross-talk". As shown, tube 58 defines an aperture 60 for passage of the light signal 34 in a direction of the turning mirror 24. As further shown, a conical extension 58A of the tube 58 can be placed after the mirror 24 in a direction of the detector 30. A thickness of the tube 58 is minimized.

Also shown in FIG. 2, the tube 58 can have specular interior and exterior surfaces as well as a highly reflective coating 58B, such as gold, applied by electrolysis deposition, evaporation or other thin film coating method. The coating 58B reflects rays 34, 46 that would ordinarily terminate at a surface of the tube 58 back into respective optical paths from which they came. Although an image of the illumination source 14A, 14B may be vignetted, the "lost" light in the image is still focused to a spot within the zone illuminated by the illumination source 14A, 14B. Likewise, the returning light outside the tube 58 can be kept from being lost by traveling inside an outer tube with a specular reflecting surface (not shown, but surrounding the outer light path). This will keep light loss to a minimum while keeping the input and output paths relatively isolated from one another.

As introduced above, the reflected light 46 shown in FIGS. 1 and 2 travels back down the outer annular region 42A of the sampling tube 22, past the turning mirror 24. The light 46 reaches the beam splitter 28 (one of its operating positions shown in phantom). The beam splitter 28 divides the light 46 with a neutral or gray spectrum, sending some of the light 46 in a direction of the first or Multivariate Optical Element (MOE) detector 30 through the MOE 48, briefly introduced above, and through a first lens 50 onto the photo detector 52, also briefly introduced above. Beam splitter 28 sends some other portion of the light 46 through a second lens 54 onto the other detector 56, also briefly introduced above.

As shown in the following table by way of example, but not of limitation, some detectors suitable for use as the detectors 52, 56 include:

TABLE 2

| Detector | Types[1] | Wave Range ($\lambda\mu$) | Detectivity $D^2$ | Cut Off Frequency ($H_z$) | Operating Temperature (K) |
|---|---|---|---|---|---|
| Pt—S | PV | 0.35-0.6 | 30 | $10^8$ | 295.0 |
| Si p-n PD | PV | 0.4-1.0 | 50 | $10^7$ | 295.0 |
| Si p-i-n PD | PV | 0.4-1.1 | 80 | $10^8$ | 295.0 |
| Si APD | PV | 0.4-0.8 | 80 | $10^{10}$ | 295.0 |
| Ge p-n PD | PV | 0.6-1.8 | 50 | $10^7$ | 295.0 |
| InSb p-n PD | PV | 3.0-6.2 | 8 | $5 \times 10^2$ | 77.0 |
| PbSnTe p-n PD | PV | 5.0-11.4 | >15-60 V/W | 10 | 77.0 |
| PbS | PC | 0.5-3.8 | 15.00 | 300 | 196.0 |
| PbSe | PC | 0.8-4.6 | 3.00 | $3 \times 10^3$ | 196.0 |
| PbTe | PC | 0.8-5.5 | 0.16 | $3 \times 10^3$ | 196.0 |
| p-InSb | PC | 2.0-6.7 | 2.00 | $2 \times 10^5$ | 77.0 |
| n-InSb | PC | 1.0-3.6 | 30.00 | $2 \times 10^6$ | 195.0 |
| PbSnTe | PC | 5.0-11.0 | 1.7 | $8 \times 10^5$ | 4.2 |
| CdHgTe | PC | 5.0-16.0 | 3.00 | $10^4$ | 4.2 |
| Ge: Au | PC | 2.0-9.5 | 0.02 | $10^4$ | 77.0 |
| Ge: Zn, Au | PC | 5.0-40.0 | 1.00 | $10^3$ | 4.2 |
| Ge: Cu | PC | 5.0-30.0 | 3.00 | $10^3$ | 4.2 |
| Si: Al | PC | 2.0-16.0 | 1.00 | $10^4$ | 27.0 |
| Si: Sb | PC | 2.0-31.5 | 1.80 | $10^4$ | 4.0 |
| ATGS | TC | 1-1000 | 0.030 | 10 | 295.0 |

TABLE 2-continued

| Detector | Types[1] | Wave Range (λμ) | Detectivity D[2] | Cut Off Frequency (H$_z$) | Operating Temperature (K) |
|---|---|---|---|---|---|
| (Ba,Sr)TiO$_3$ | TC | 1-1000 | 0.011 | 400 | 295.0 |
| Si | — | 0.2-1.1 | — | — | — |
| Ge | — | 0.4-1.8 | — | — | — |
| InAs | — | 1.0-3.8 | — | — | — |
| InGaAs | — | 0.8-3.0 | — | — | — |
| InSb | — | 1.0-7.0 | — | — | — |
| InSb (77K) | — | 1.0-5.6 | — | — | — |
| HgCdTe (77K) | — | 1.0-25.0 | — | — | — |

Note 1:
PV—photo transistor type; PC: photo conductive detector type; TC: pyroelectric detector type Note 2:
($10^{10}$ cmHz$^{1/2}$ W$^1$)

As further shown in FIG. 1, a gain mechanism 64 is in communication with the detectors 30, 32 and the MOE 48. The gain mechanism 64 weights a magnitude of the property of an orthogonal component of a portion of the carrier light 48 as described, for instance, by Myrick et al. in U.S. Pat. No. 6,198,531 B1 and in U.S. Pat. No. 6,529,276 B1 to Myrick.

As briefly introduced above, beam splitter 28 is not required in an alternative embodiment of the present subject matter in which a signal from the sample W is analyzed using a PCR-type model in an off-line approach. This alternative embodiment and approach is useful, for instance, for studying signals independently. More particularly, a system substantially as described above but without the beam splitter 28 is used to take an integral of the light on a detector similar to the detector 30 described above. By analyzing frequency-dependent intensities, results similar to those of the foregoing embodiment are produced, although possibly with a relatively slower response time in the present embodiment.

Also, in an additional aspect of the disclosure as shown in FIG. 1, a system 68 using an electrochemical or chemometric model can be employed in conjunction with any of the foregoing embodiments to make similar or same measurements of the light 46 reflected from the sample W as the measurements described in the foregoing embodiments. By way of example but not of limitation, the system 68 may be one as described by Myrick et al. in PCT Application Number PCT/US2004/043742, based on U.S. Provisional Application No. 60/533,570, filed Dec. 31, 2003, which are incorporated herein by reference thereto.

In addition to the reflectance mode described above, one or more optical analysis systems can operate in a transmission mode in conjunction with the foregoing embodiments. In such a case, light is directed (passes) through the sample W, e.g., a fluid sample, and collected on another side of the sample W to enable study of particle density in the fluid in conjunction with the chemical content described above. For instance, the system 10 can be configured to operate in transmission mode where the light is shone through the sample W to a similar detection system 110 as shown in FIG. 1 in phantom for clarity). Additionally, or alternatively, a mirrored surface 210 can be placed within the transmissive sample W to reflect the light back into the system 10.

With reference now to FIG. 3, a second exemplary embodiment of the present subject matter is designated generally by reference number 110. Many aspects of the optical analysis system 110 and related components are similar to the foregoing embodiment; thus, for the sake of brevity, only certain differences are described below. However, to provide a full and enabling disclosure of the optical analysis system 110, when like or similar elements and components are not specifically described below; implicit reference is made to the foregoing descriptions.

As shown in FIG. 3, the optical analysis system 110 broadly includes a housing 112, an illumination or light source 114, a chopper wheel 118, one or more spectral elements 120, a beam splitter 128, a first detector 130 including a multivariate optical element 148, and a second detector 132. The optical analysis system 110 further includes an electrical connection 160, a pressurization sensor 162 and a purge gas assembly 164, which those of ordinary skill in the art will readily understand; therefore, further description is not necessary to understand and practice these aspects of the disclosure.

With more particular reference to FIG. 3, the illumination source 114 provides a light 134, which passes through a collecting Fresnel lens 116A and into and through the spectral element(s) 120. In this example, the illumination source 114 is rated for at least about 10,000 hours of operation, which alleviates a need for redundant illumination sources though they may be provided if desired. Also in this example, the collecting Fresnel lens 116A is sized to be about 1.5 square inches and is spaced about 0.6 inches from the illumination source 114. Those of ordinary skill in the art will recognize that these dimensions can be adjusted according to particular system requirements and are not meant as limitations of the disclosure.

As further shown in FIG. 3, light 134 passes through the spectral elements 120, which filter out undesired wavelengths to define a desired spectral region, e.g., 1500-2000 nm, in order to target a particular chemical material of interest. Light 134 is focused by focusing Fresnel lens 116B, which may also sized to be about 1.5 square inches and spaced about 1 inch from chopper wheel 118. As shown, chopper wheel 118 reflects a portion of light 134 as a calibration or reference light 135 and a transmitted light 144. Calibration light 135 is collimated by lens 158 before reflecting from a first mirror 124A through an adjustable aperture 112B in a bulkhead 112A of the housing 112. Aperture 112B is adjustable to dictate a desired amount of the calibration light 135. Finally, calibration light 135 impinges on beam splitter 128 thereby sending a portion 135A of calibration light 135 to the first MOE detector 130 and a portion 135B of calibration light 135 to the second or baseline detector 132.

FIG. 3 further illustrates that transmitted light 144 passes from chopper wheel 118 into collimating Fresnel lens 136, which in this example is sized to be about 1.5 square inches and is spaced about 0.6 inches from chopper wheel 118. The transmitted light 144 passes through another adjustable aperture 112C in bulkhead 112A and impinges upon a second mirror 124B, which directs transmitted light 144 toward sample M in a container C, such as a mixing vat or blender. Those of ordinary skill in the art will recognize that the container could be a conveyor belt or other device for holding or transporting the sample M and is not limited to an enclosed container.

Figure 5:
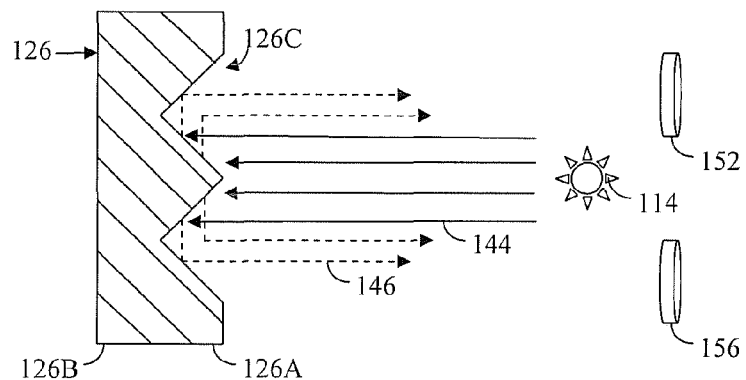
FIG. 5 is a cross section of the retroreflecting mirror taken along line V-V in FIG. 4B.

As shown in FIG. 3, transmitted light 144 passes through transmissive window 113 and enters container C and on through sample M. Sample M may be a substantially transparent liquid, such as water, petrochemicals, or the like but can also be any relatively clear product such as gelatin capsules containing a pharmaceutical product. As shown, focusing lens 126, which in this example may be round in shape, may be positioned adjacent to or as much as one inch from an outer surface of container C. Transmitted light 144 passes through sample M and reflects from focusing lens 126 as a carrier light 146. Further details of focusing lens 126 are described below with respect to a similar lens 226 as shown in FIGS. 4A, 4B and 5.

Continuing with reference to FIG. 3, carrier light 146 may be directed by tube 122 in a direction of the first detector 130. Eventually, carrier light 146 impinges on beam splitter 128 and a portion passes in a direction of detector 132 for baselining with the portion 135B of calibration light 135. Another portion of carrier light 146 passes through MOE 148, which as noted above, has been selected for the chemical of interest based on the various components of system 110. Finally, that portion of carrier light 146 having passed through the MOE 148 is focused by lens 150 and received by detector 152. As described above, the two signals collected by detectors 132, 152 can be manipulated, e.g., mathematically, to extract and ascertain information about the sample carried by carrier light 146.

Figure 4A:
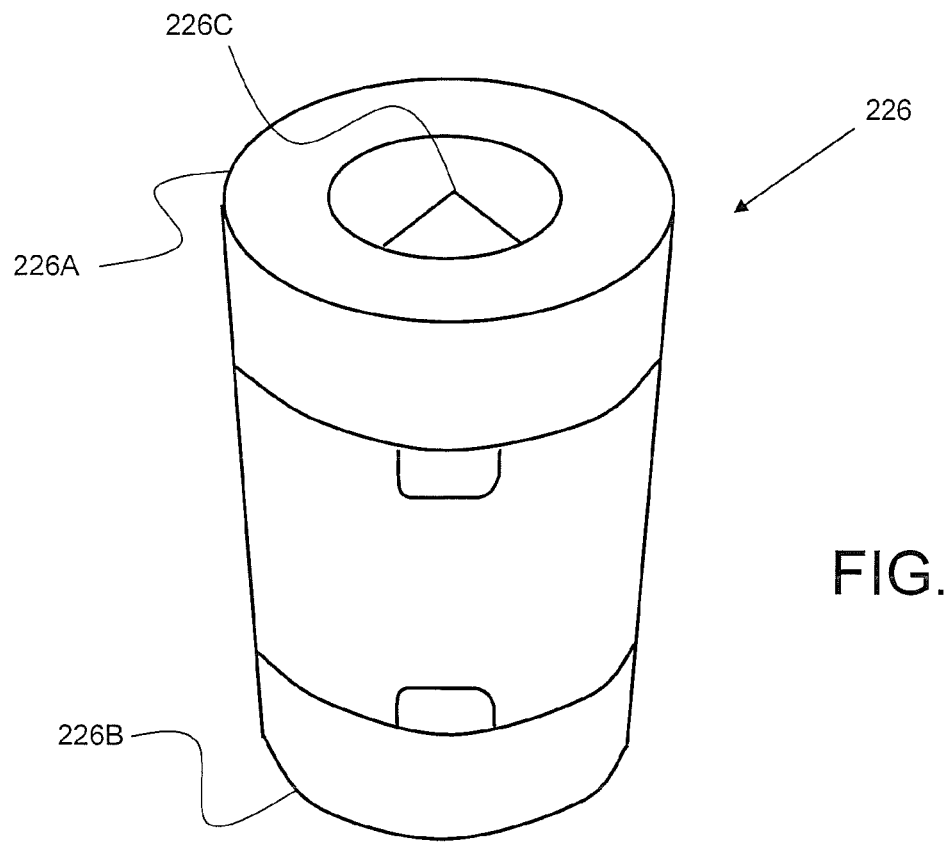
FIG. 4A is a perspective view of a retroreflecting.
Figure 4B:
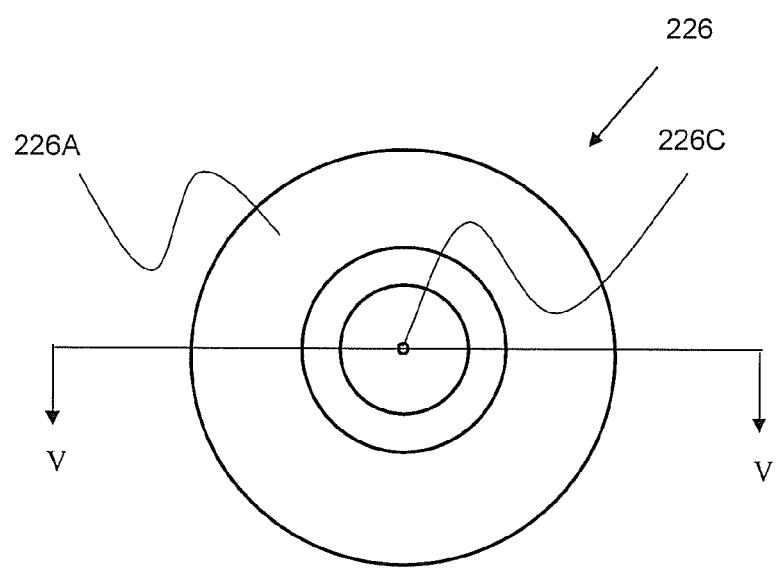
FIG. 4B is an end view of the retroreflecting mirror of FIG. 4A.

Turning now to FIGS. 4A and 4B, detailed views of a retroreflector or collimating mirror 226 are shown. In this example, mirror 226 is similar to mirror 126 and is generally cylindrically shaped with a first end 226A and a second end 226B. Mirror 226 is also coated with a reflective surface such as aluminum (Al), gold (Au) or other elements and/or materials or combinations thereof as dictated by the desired spectral region. Those of ordinary skill in the art will appreciate that other shapes and reflective coatings can be provided to meet specific design requirements and characteristics of the target sample; thus, mirror 226 is not limited to the exemplary embodiment shown in FIGS. 4A and 4B.

With reference to FIGS. 3, 4A and 4B, mirrors 126, 226 are useful for analyzing translucent liquid samples. For example, since liquids, in contrast to powders, do not readily create a diffuse reflectance to produce the desired carrier light 146 as shown in FIG. 3. By way of example operation, lens 126 in FIG. 3 may be removed and replaced with mirror 226 for retroreflection of light 144 for transreflection measurement of carrier light 146 for liquid sample analysis.

Turning now to FIG. 5, as light 144 passes through mirror 126, the light is collimated into the liquid sample in container C as in FIG. 3. As shown in FIGS. 3 and 5, carrier light 146 reflects from the liquid sample and returns through the first end 126A, which defines one or more conical shaped depressions or indentations 126C. The conical shaped indentations 126C act to diffuse the carrier light 146, and the carrier light 146 is directed through the MOE 148 as described above.

Figure 6:
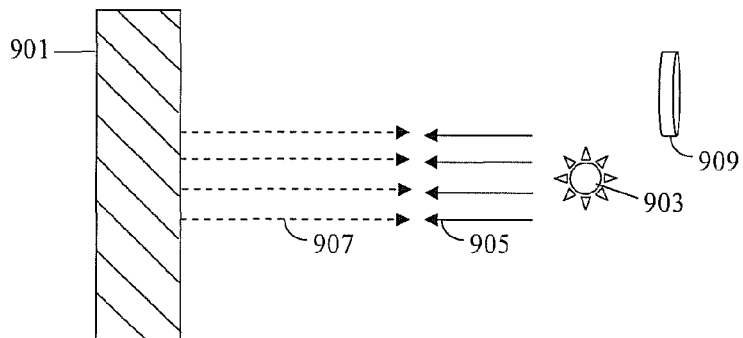
FIG. 6 is a cross section of a conventional mirror.

In contrast to the embodiment of the present subject matter illustrated in FIG. 5, a conventional flat mirror 901 and light 903 are arranged in a conventional manner as shown in FIG. 6. Light 903 shines light rays 905 in a direction of the flat mirror 901, which reflects light rays 907 along the same ray path as the emitted light rays 905. Accordingly, any information carried by the light rays 907 reflecting from the flat mirror 901 would at least interfere with the light 903 and possibly be unreadable by a detector 909 offset from the light 903 due to interference with the light rays 905.

Those of ordinary skill in the art will appreciate that the disclosure is not limited to the foregoing exemplary arrangements. For example, the system can be arranged with mirror 126 and detectors 152, 156 on an opposite side of the container C such that light 146 passes through the liquid sample into mirror 126. Accordingly, in this alternatively embodiment, particle density in a fluid can be studied in conjunction with a chemical content of the fluid.

The functionality of the MOC system 10 or 110 as described above allows for the collection of the entire spectral range of testing simultaneously, i.e. the present disclosure provides for dynamic real-time detection and measurement. This is notably different than either a system based on either a scanning lamp or detector system or a discrete diode array detection system. The ability to monitor over the complete spectral range of interest opens up a re-definition of the term "real-time" measurement and analysis.

For instance, true "real-time" process measurements are possible where "real time" refers to obtaining data without delays attendant to collecting samples or delays due to lengthy computer processing of measurement signals. For example, in exemplary methods described below, process data can be obtained in an instantaneous or near-instantaneous manner through using measurement techniques to directly monitor materials of interest while such materials are undergoing process steps. Long delays due to processing of measurement signals are avoided by optically processing the light as it is reflected from the material(s) of interest.

Although specific examples disclosed herein present monitoring the blending of a powdered material and examining solid tablets, the concept can be extended to other phases as briefly introduced above. Thus, the present systems and methods can be utilized to analyze solids, solutions, emulsions, gases, dispersions and the like. In addition, while exemplary embodiments discussed herein use reflectance measurements, measurements in a transmission or transflectance mode would also be appropriate.

One of ordinary skill in the art will recognize that differing applications may require modifications and alterations to certain components in order to take full advantage of the presently disclosed systems. For instance, more diffusion of light has been observed in solid powders relative to liquids; accordingly, different lenses may be needed when a liquid is monitored in order to account for such variations and achieve more accurate measurements.

The presently disclosed technology can be applied to real-time measurements for a range of industrial applications. These include, but are not limited to monitoring of the blending of pharmaceutical powders, including excipients, additives, and active pharmaceutical materials; blending of other powders, including food and chemicals; monitoring dispersions and bi-phasic mixtures such as, but not limited to, insulin and emulsions; and oil and gas applications, including analyzing water content in oil, or oil content in water.

Inclusion of a transmissive window provides physical separation between the measuring device and the process or material being tested. Therefore, this window allows for in-line measurement and/or non-invasive measurement of parameters such as chemical functionality, including alcohol content of petroleum fractions or tackifier resins. Environmental applications of the present subject matter include, but at not limited to, stack gas analysis including measurement of NOx, SOx, CO, CO2, or other gases in a gas stream; wastewater analysis and treatment monitoring; and hazardous substance monitoring applications such as mercury vapor detection.

As noted above, MOC technology can be used to monitor a wide variety of materials as the materials are subjected to different processes. For instance, the mixing of powders can be monitored. As materials are blended, the existing art does not allow for continuous, real-time, in-line measurement. Current limitations are the result of several factors including: moving of the powders being measured during the course of data acquisition and the need to connect analytical equipment to the measurement point using fiber optic cables. This optical analysis system is designed to allow for instantaneous measurement using a measurement point located on the vessel.

Figure 7A:
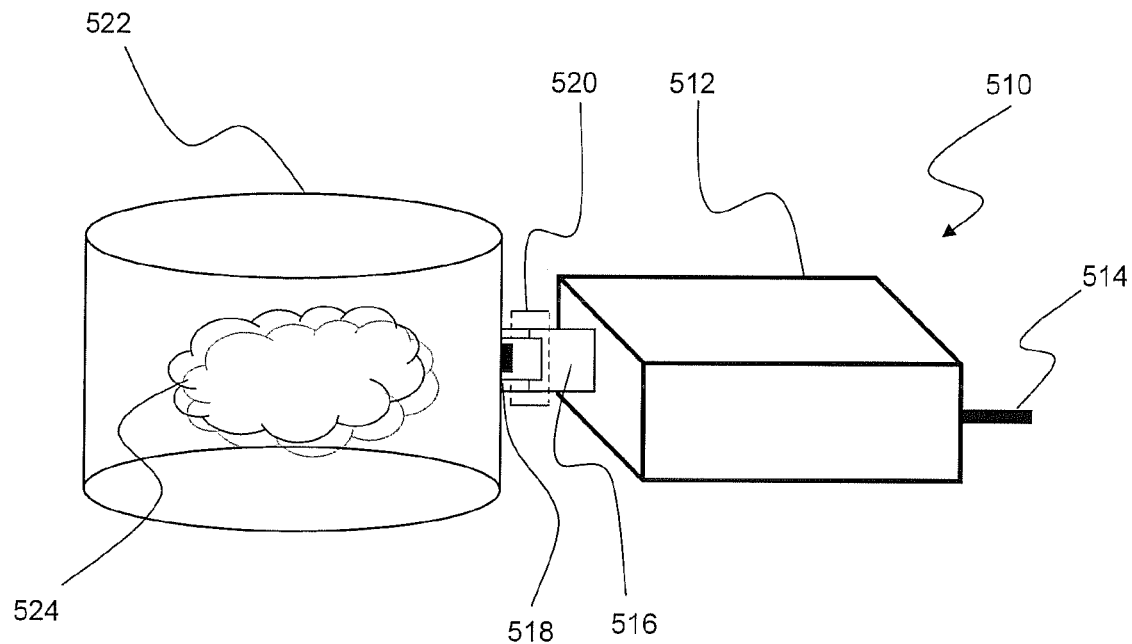
FIG. 7A is a schematic view of an implementation in which a material may be measured in real-time.

To measure the composition of the mixture of powders during blending, the system is located in a position to shine the sampling beam into the mixture. An exemplary implementation of such a measurement technique is illustrated in FIG. 7A. An optic head 510 includes a housing 512 and requisite MOEs and spectral elements to obtain desired information about a material of interest. The optic head 510 is generally configured and constructed in accordance with the embodiments discussed above in conjunction with FIGS. 1-5.

In discussing various embodiments below, the term "optic head" is used in place of the term "measurement system" in referring to the light, lenses, spectral elements, and detectors of the optical computing unit discussed above. As will be apparent to those of ordinary skill in the art, a complete measurement system may utilize several instances of the optical computing unit, and so the term "optic head" is used as a shorthand reference to a single instance of the optical computing unit.

With more particular reference to FIG. 7A, the optic head 510 is connected via an umbilical 514 to an appropriate power supply and analysis computer or computers (such as system 68 described above) also configured in accordance with the principles of MOC analysis. As shown, a process point including a mixing blender bowl 522 containing mixture 524 may thereby be monitored via the optic head 510.

FIG. 7A further shows a port or connection 520 such as a Swagelok® brand pharmaceutical-grade stainless steel port introduced above. Connection 520 connects opening 518 of the mixing blender bowl 522 to optic head inlet 516. Inlet 516 includes the window (13 or 113 in the embodiments discussed above) through which light is transmitted and reflected for materials analysis while keeping the material monitored separate from the internal components of optic head 510.

Figure 7B:
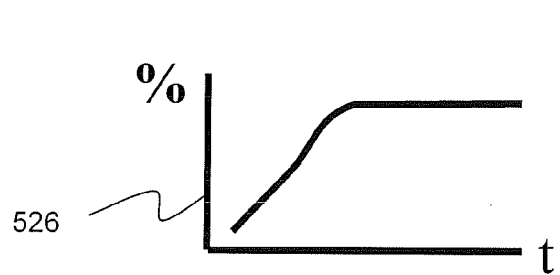
FIG. 7B is an exemplary concentration graphical representation of measurements over time obtained from an exemplary device constructed in accordance with the present subject matter.

By way of example, optic head 510 in FIG. 7A can be configured to monitor the concentration of a mixture of aspirin and lactose. Accordingly, a sapphire window (e.g., window 113 in FIG. 3) may be positioned at the end of optic inlet 516 for interrogating the powder, and optic head 510 may be configured with MOEs designed to monitor aspirin concentration. More specifically, a 20-watt Gilway lamp may be modulated using 5 mm $D_2O$ and 5 mm Germanium spectral elements, and the modulated light may be directed into the powder. The reflected light from the powder is directed through the MOEs onto a PbS detector. A portion of the modulated light, as discussed above, is preferably directed into a second detector. The resulting PbS detector signal can be compared against the second detector signal in order to determine the concentration of aspirin. For example, a concentration graph 526 as shown in FIG. 7B may be obtained, which shows a rise in aspirin concentration as aspirin is added. FIG. 7B further shows a "leveling-off" (asymptote phenomenon) as the mixing process continues.

Those of ordinary skill in the art will appreciate that other embodiments in which transmitted light is to be measured would utilize two ports, preferably located opposite one another with the measured sample passing between the two ports.

Other embodiments of the present subject matter include real time measurement of flowing materials. In such embodiments, the sampling window(s) may be located on a pipe or vessel such that interrogating illumination can be applied to the material. For instance, a port similar to the port 520 in FIG. 7A could be included on a pipe to allow for sampling of the material inside the pipe. A window as described above may be positioned directly on the pipe, or on a small diversion away from the main flow path, as appropriate under certain circumstances. Such embodiments could also include sampling of vapor systems within a stack to monitor combustion gases or flowing process stream such as water containing other materials.

Still further embodiments of the present subject matter include the real time measurement of materials in containers, such as vials or bins where the container is either at least partially open to the outside environment or transmissive to the sampling illumination. Such containers could be stationary or in motion. A container could also include a conveyor or trough carrying material. Typical applications could include the monitoring the progress of a chemical reaction or the content of samples moving past a measurement location.

Figure 8A:
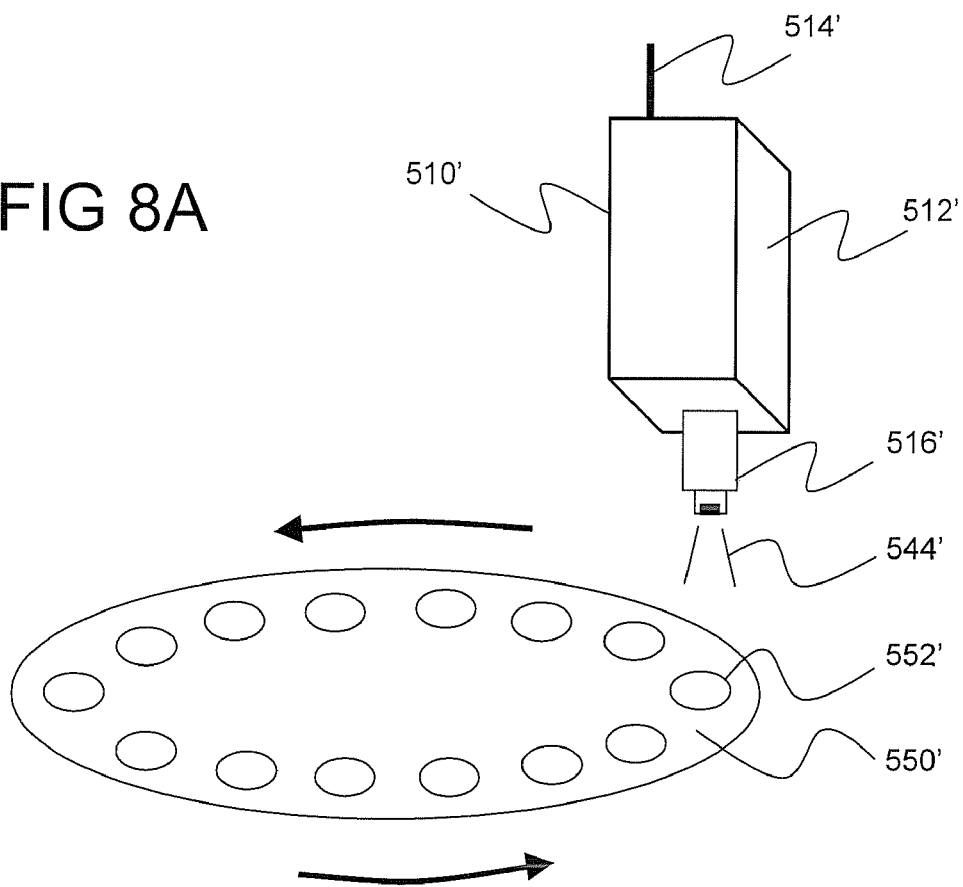
FIG. 8A is another exemplary schematic view of a real-time process measurement using an exemplary device constructed in accordance with the present subject matter.

For instance, FIG. 8A illustrates a plurality of samples 552' positioned on a rotating disc conveyor 550'. Although a disc conveyor is shown, one of ordinary skill in the art will recognize that the samples 552' may be positioned on a conveyor belt or other automated conveyance, depending upon the particular testing circumstances and environment. Also, although the samples 552' are illustrated as tablets in FIG. 8A, the samples 552' could be or include capsules, caplets, pills, and other individualized units of pharmaceutical product or other consumable product.

As further shown in FIG. 8A, tablets 552' are rotated into the view of optical inlet 516' of optic head 510', which is similar to the discussion above and may include a housing 512' and an umbilical 514', as well as requisite internal components, filters, and MOEs to perform the desired testing operations. Likewise, this exemplary system and process may be configured to monitor around five tablets per second, with the tablets 552' being in continuous motion.

Figure 8B:
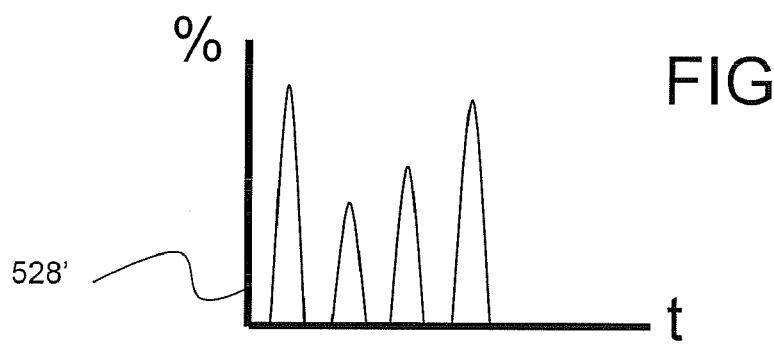
FIG. 8B is an exemplary graphical representation of measurements over time obtained from the exemplary device of FIG. 8A.

As discussed in conjunction with the optic head 510 in FIG. 7A, in the embodiment of FIG. 8A, a PbS detector can be used in conjunction with a sapphire window and D20 and germanium spectral elements to monitor the concentration of aspirin and lactose. In contrast to the system of FIG. 7A, the sapphire window of optic inlet 516' is positioned above the samples 552' such that a beam of light 544' is focused downward onto samples 552' on the conveyor 550'. However, the optical principles described above remain the same. As shown in FIG. 8B, a graph 528' represents exemplary results that would be obtained from the samples 552' of varying concentration of aspirin, with each spike representing an individual one of the samples 552' being in full view of optic head 510'.

Samples 552' may be actual samples to be measured, such as the tablet end product illustrated in FIG. 8A and discussed below in conjunction with FIG. 9. However, one of ordinary skill in the art will recognize that samples 552' may also include transparent containers and the like, which may contain a dispersion or suspension of a solid material in a liquid or a solution, or solid materials. For instance, trays of powder can be placed on an automated conveyance and brought into view of optic head 510' in a manner similar to the method described in FIG. 8A.

Additionally, instead of moving samples 552', one of ordinary skill in the art will note that measurement device 510' could be repositioned to examine samples 552' by appropriate machinery such as overhead tracks, robotic arms, and the like. Those of ordinary skill in the art will recognize that in such cases, appropriate care would preferably be taken to ensure that force levels applied to the measurement device and its internal components remained within tolerable levels.

Figure 9:
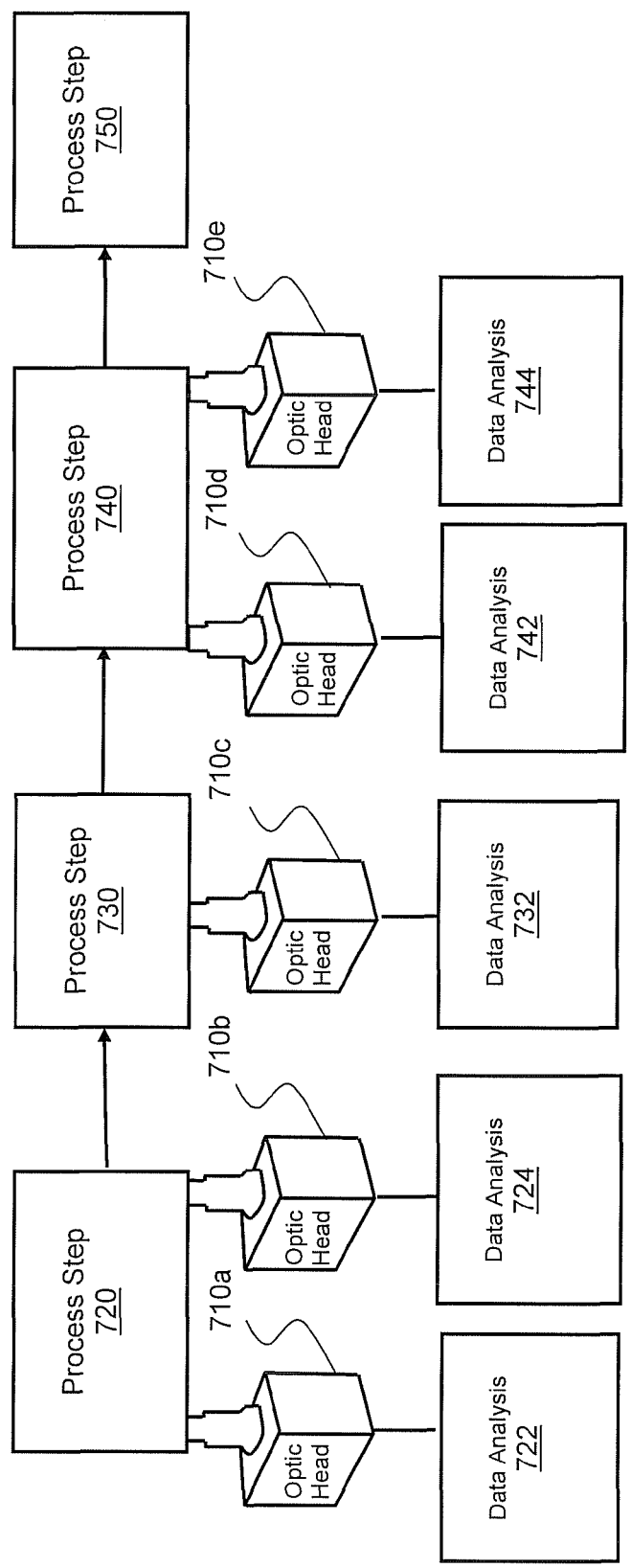
FIG. 9 is a schematic view of multiple process stages for monitoring material characteristics according to the present subject matter.

Turning now to FIG. 9, an embodiment of real-time process management using MOC systems in accordance with the present technology is schematically depicted. As shown, a plurality of optic heads 710a-e are integrated into various process steps 720, 730, and 740. Process steps 720, 730, and 740 can represent stages or steps of any number of industrial operations in which materials are handled or manipulated, and in which physical state or compositional data is desirable. In accordance with the system embodiments discussed above, each optic head 710a-e is provided with MOEs and other optical components specifically tailored to the materials characteristics, which are to be monitored at each step, and interfaced with process control computer(s). The analysis data ultimately provided by collection points corresponding to optic heads 710a-e are shown at 722, 724, 732, 742, and 744. Such data can be obtained using single or multiple process control computers configured to collect, analyze, and otherwise handle the data from the detectors within the optic heads in accordance with the principles of multivariate optical computing discussed above.

Assume, for example, that process steps 720, 730, and 740 represent various stages in a pharmaceutical manufacturer's production line for blending powder and forming tablets. Those of ordinary skill in the art will recognize that pharmaceutical manufacturing often entails strict control and monitoring of material composition and mixing at every stage of production.

The initial steps of obtaining and readying component materials in a pharmaceutical process could be represented at 720 in FIG. 9. Optic head 710a could be used to monitor the incoming raw materials in trays or on conveyors and provide inspection and quantification data 722, such as purity data. Optic head 710b could be configured to the monitor incoming material(s) as they undergo an initial process stage, for example, providing chemical drying characteristics 724 as the raw materials are dried.

Process step 730 in FIG. 9 could represent mixing of active and excipient components into a powder, and optic head 710c could provide data 732 on mixing progress. For instance, optic head 710c could be interfaced with the mixing container and provide data tracking active ingredient concentration over time as in FIG. 7B. Based on such concentration, requisite steps could be taken to ensure the optimal amount of active component is in the resulting mix or otherwise adjust the mixing process by altering temperature or the like.

As further shown in FIG. 9, step 740 could represent pressing tablets, with optic heads 710d and 710e positioned above a conveyor moving the completed tablets, and providing data 742 on tablet components and homogeneity, as well as data on coating thickness and uniformity 744.

FIG. 9 further shows a step 750 representing the final portions of the manufacturing process, which are not monitored, such as packaging. One of ordinary skill in the art will recognize, however, that step 750 could represent the entry into a different process, which is itself monitored by one or more optical analysis systems as described herein.

Figure 10:
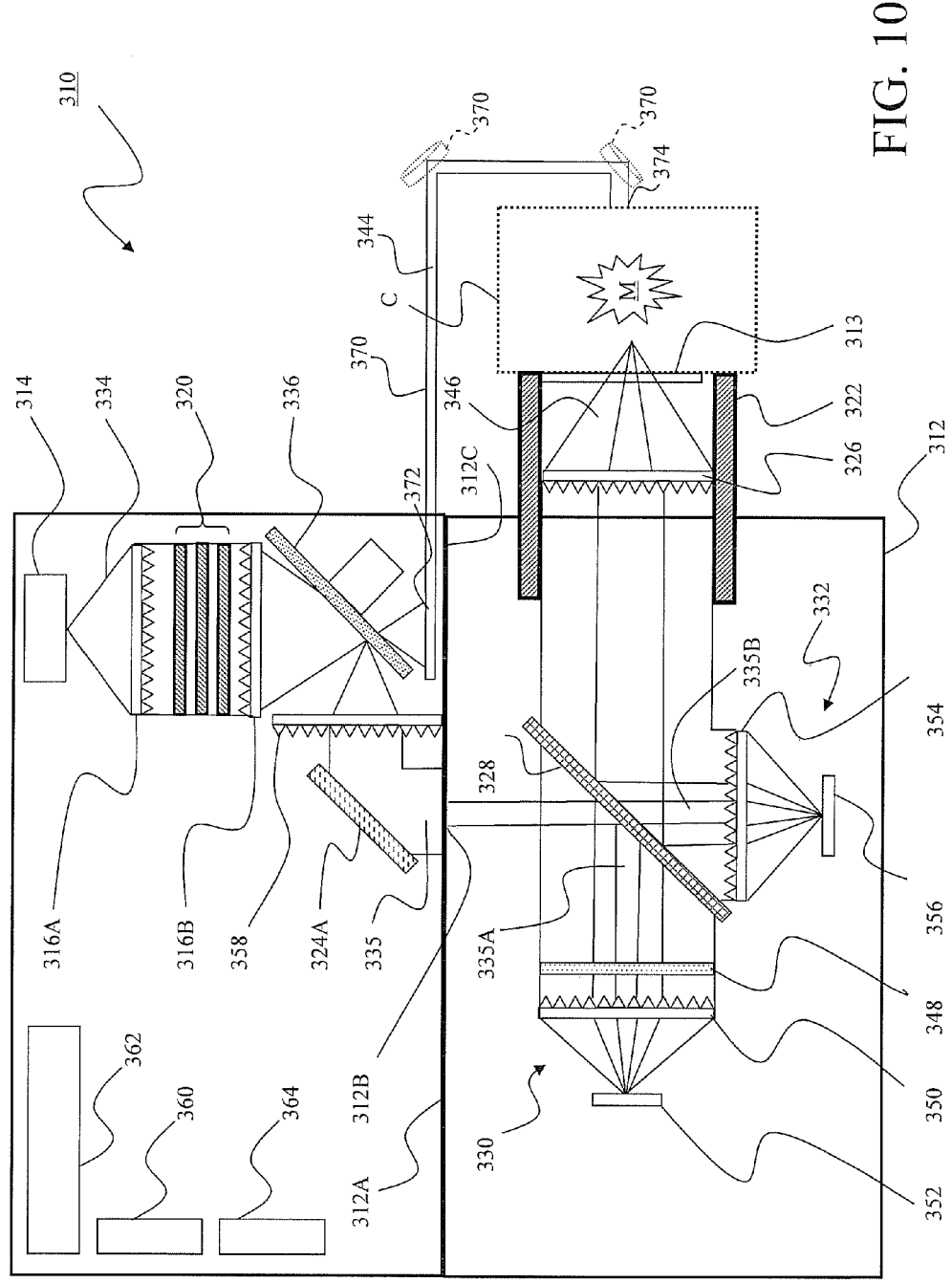
FIG. 10 is a schematic plan view of another exemplary embodiment of a real time measurement system constructed in accordance with the present subject matter.
Figure 11:
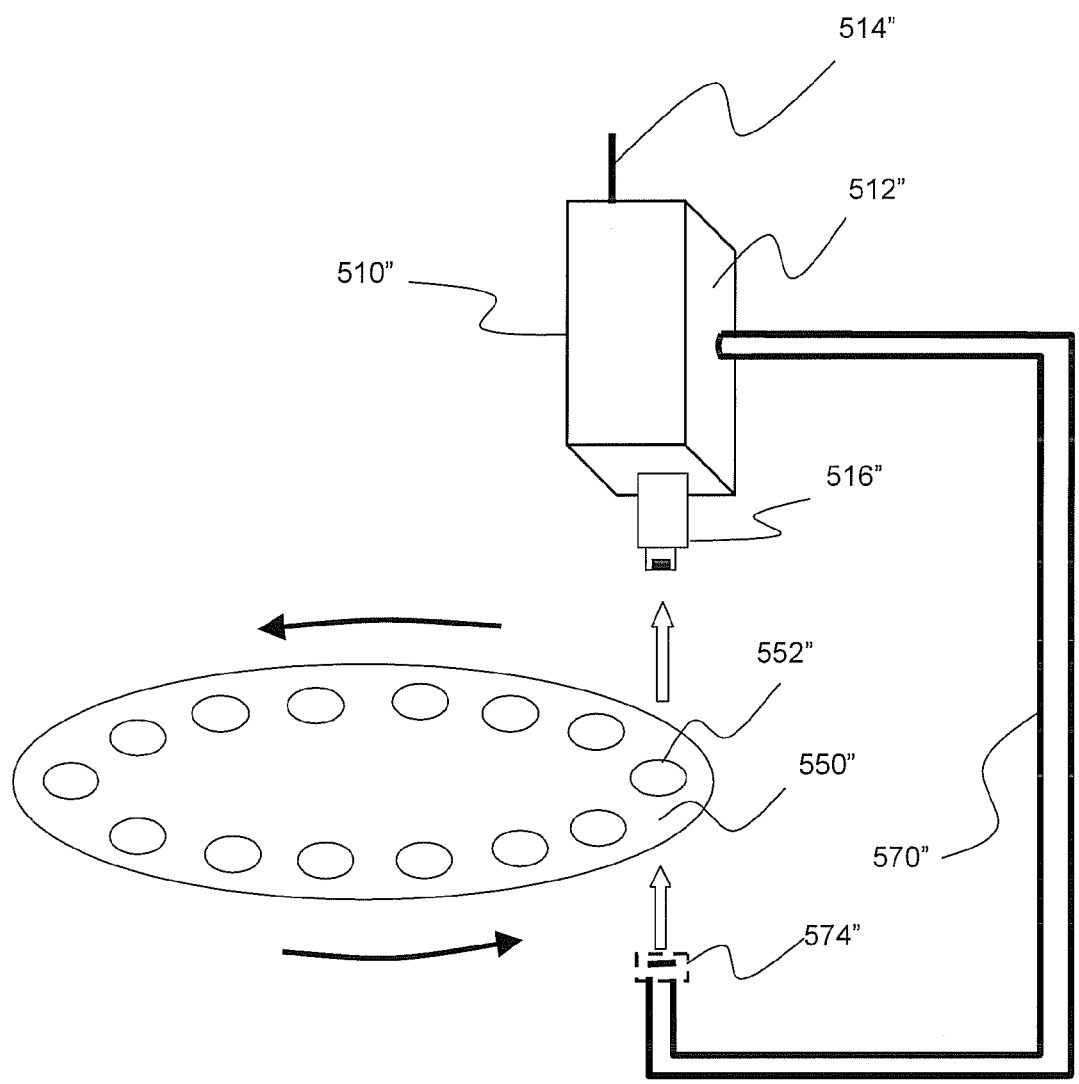
FIG. 11 is a schematic view of an exemplary measurement process according to a further embodiment of the present subject matter.
Figure 13A:
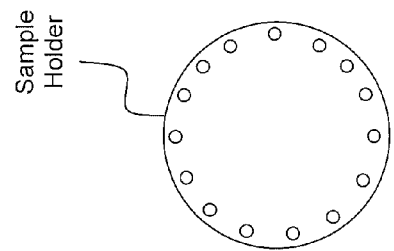
FIGS. 13A and 13B are respectively top and side portion views of an exemplary sample holder showing placement of a sample tablet into the sample holder.
Figure 13B:
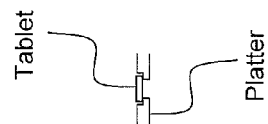

Attention is now directed to the exemplary embodiments of the present disclosure as illustrated in FIGS. 10 and 11. Those of ordinary skill in the art will note that prior exemplary embodiments discussed reflective measurements, while noting such embodiments could be suitably configured for use in transmissive measurement schemes. FIGS. 10 and 11 illustrate examples of such configurations.

In FIG. 10, for instance, a multivariate optical measurement system 310 is configured in a manner similar to the embodiment discussed with respect to FIG. 3, above. However, a light diversion path 370 in one embodiment includes a fiber-optic cable having ends 372 and 374 has been included to divert light 344 emanating from a source 314 into the tested material M such that light 344 is transmitted through material M and into the remaining elements, i.e. detectors, MOEs, etc. The light diversion path is not limited to a fiber optic cable and could be mirrors in series, as shown in phantom for clarity.

As shown in FIG. 10, light 344 enters end 372 of diversion path 370 after passing through Fresnel lenses and spectral elements 320 and modulating chopper wheel 318. However, one of ordinary skill in the art will recognize that the point of diversion may be varied according to the particulars desired in a system. For instance, the beginning 372 of path 370 could be placed on the other side of optional aperture 312C. Also, although a collimating lens such as collimating lens 136 of FIG. 3 is not shown in FIG. 10, such a lens, or other suitable optical components, could be placed at end 372 of path 370 to appropriately condition light 344 for optimal measurement via transmission through material M. Similarly, optical components, such as a focusing lens or a spectral element, could be included at diversionary path outlet 374; such placement is illustrated by element 574" shown in phantom in FIG. 11 and further described below. Moreover, path 370 in FIG. 10 could include other means and methods for directing the path of light, such as the above-described fiber optic cable, mirrors, or a variant of the tube and mirror combination discussed in conjunction with other embodiments of the present disclosure, for example.

As further shown in FIG. 10, light 346 transmitted through material of interest M passes through window 313 and lens 326 and into the remaining components of the multivariate optical system in a manner similar to the foregoing descriptions. Depending upon the particular implementation of a measurement system, window 313 and/or lens 326 may be varied or removed depending upon the light intensity and focus that is needed to optimize measurements by detectors 352 and 356.

Turning now to FIG. 11, an implementation of transmissive measurement using diverted illuminating light is shown. As discussed previously in conjunction with FIGS. 7A and 8A, portions of a measurement system may be adapted for housing within an optic head as described above. Thus, an optic head 510" may be internally configured with lamps, spectral elements, MOEs and the like in accordance with the principles of multivariate optical computing and measurement. As shown in this example, optic head 510" includes housing 512" and inlet point 516".

Optic head 510" in FIG. 11 is further adapted to house an optical measurement system such as the one discussed above in conjunction with FIG. 10 to route illuminating light into a material opposite the inlet point 516" to allow for transmissive measurements using optic head 510". As shown, an exemplary diversion path 570" runs from optic head 510" to an output point 574". Light is transmitted through sample 552" (corresponding to material M of FIG. 10) and into inlet point 516" of the optic head 510" for optical processing and detection. One of ordinary skill in the art will recognize that the conveyor disc 550" would be configured such that light emitted from 574" is not blocked.

As noted previously, ghosted portion 574" indicates optional light conditioning and/or other interface components that may be appropriate for a particular implementation. For example, depending upon the sample 552" analyzed, different focal points may be selected using a focusing lens positioned at 574". If the sample 552" comprises a pill, the light can be focused at the center of the pill for determining composition, or at the periphery of the pill to analyze the content of a coating. Lenses of different focal lengths could be selected depending upon the particular geometry and measurement needs.

Although a plurality of discrete samples resting on a conveyor is illustrated in FIG. 11, the principles illustrated are applicable to other phases and configurations of materials. For example, ghosted container C of FIG. 10 could be substituted for the conveyor 550' of FIG. 8A for measurement of material M disposed in a mixer, pipe, or other vessel in a manner similar to that shown in FIG. 7A. In such configurations, optic head inlet point 516" (including window 13, 313) would be proximate to the pipe or mixer wall, and could be interfaced using a port or connector such as the port 520 discussed in conjunction with FIG. 7A. In such embodiments, endpoint 574" could comprise an additional port and window to directly interface the end of path 570" with the container C so that light exiting path 570" would travel through the material in the container and then into inlet point 516". In that manner, real-time transmissive measurement of continuous processes is conceivable.

Figure 12:
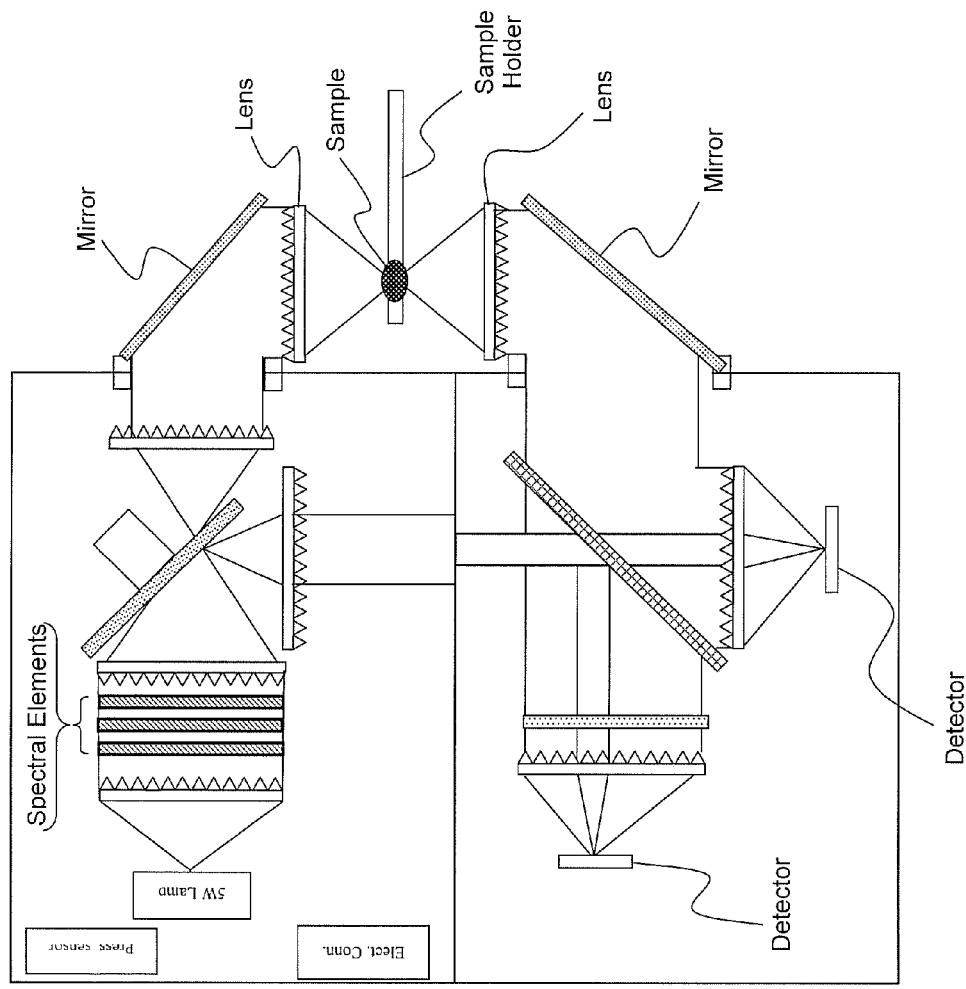
FIG. 12 is an exemplary configuration of a measurement device constructed in accordance with the present subject matter for a transmission system configured to measure tablets.

FIGS. 10 and 11 show schematic layouts of a transmission measurement system. FIG. 12 shows a schematic layout of a transmission system using mirrors and lenses to direct the light from the Gilway lamp to the sample and to the detectors. The light is produced by the lamp and passes through the spectral elements and the chopper. A portion of the light is deflected by the chopper directly to the beam splitter and then to the detectors. This is termed the autocalibration beam.

Sample light modulated by the chopper passes through a lens, is reflected by a mirror and is focused on the sample. The lens on the light beam illuminating the sample is chosen to focus the light on an area smaller than the diameter of the sample. For a round tablet, this diameter is clear. For a non-round sample, this focusing may involve a more complicated focusing device to produce a shaped beam that corresponds to the shape of the sample. Such shapes might be square, oval, diamond or other shapes. Maintaining the light beam smaller than the sample dimensions provides a reduction in the light going around the sample.

Light that is transmitted through the sample is collected by a lens, reflected by a mirror and hits the beam splitter sending a portion of the light to one detector and a portion through the Multivariate Optical Element and onto the other detector. Light going around the sample is expected to add noise to the measurement. By minimizing noise, more reliable measurements can be made. In addition, because a portion of the sample is not illuminated, the system is not as susceptible to variations in the precise size of a given type of tablet. Previous art has required a precisely machined or laser die cut or the like as a holder for the tablet to prevent any of the light going around the tablet.

The present system enables a more reliable measurement because the system is not as subject to variability of the precise size of the tablet and/or precise size of the tablet holder. All of these things lead to an improved signal to noise ratio, which enables measurement of lower concentrations of analytes, for instance drugs at <0.05 wt %.

The present subject matter may be better understood from the following tests and examples. Example I/System I corresponded to a first breadboard system was constructed and used to test a mixture of powders and included components as follows:
  Illumination: 20 W Gilway lamp
  Spectral elements: 5 mm deuterium oxide ($D_2O$), 5 mm Germanium
  Optical window: fiber optic probe
  Detector: InAr detector from Judson
  MOE: specific to test Procedure and Results of static testing using System I: A powdered sample with a known composition was placed in a dish and the fiber optic probe was placed in contact with the powder. The output of the detectors was monitored and recorded.

Example II/System II corresponded to a system similar to the optical analysis system 10 shown in the figures was constructed and used to make static measurements on aspirin/lactose and included components as follows:
  Illumination: 20 W Gilway lamp
  Spectral elements: 5 mm $D_2O$, 5 mm Germanium
  Optical window: none
  Detector: PbS detector from New England Photoconductor
  MOE: specific to test conditions.

Procedure and Results of static testing using System II: A powdered sample with a known composition was placed in a dish and the system light beam was focused on the powder. The output of the detectors was monitored and recorded. Aspirin/lactose samples covering the range of 100% aspirin to 100% lactose were tested.

Example III/System III corresponded to a system similar to the optical analysis system 10 shown in the figures was constructed and used to make dynamic measurements on aspirin/lactose and included components as follows:
  Illumination: 20 W Gilway lamp
  Spectral elements: 5 mm $D_2O$, 5 mm Germanium
  Optical window: sapphire window
  Detector: PbS detector from New England Photoconductor
  MOE: specific to test conditions.

Procedure and Results of dynamic testing using System III: The aspirin/lactose testing was made on a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

Example IV/System IV corresponded to a system similar to the optical analysis system 10 shown in the figures was constructed and used to make static measurements on aspirin/lactose and included components as follows:
  Illumination: 5 W Gilway lamp
  Spectral elements: 5 mm $D_2O$, 5 mm Germanium
  Optical window: none
  Detector: PbS detector from New England Photoconductor
  MOE: specific to test conditions.

Procedure and Results of dynamic testing using System IV were similar to the examples above.

Example V/System V corresponded to a system similar to the optical analysis system shown FIG. 3 was constructed and used to make dynamic measurements of water/hydraulic fluid mixtures. System V components included:
  Illumination: 20 W Gilway lamp
  Spectral elements: 5 mm Germanium
  Optical window: sapphire window
  Detector: PbS detector from New England Photoconductor
  MOE: specific to test conditions.

Procedure and Results of testing using System V: Samples of automobile brake fluid were prepared with various levels of water; e.g., between 0% and 3% water. The liquid samples in quartz cuvettes with a 2 mm path length were analyzed using the system. The cuvettes were placed horizontally on a moving platter; the system was located above the platter; and the conical mirror was located below the platter.

Although various aspects of the disclosure have been described in such a way as to provide an enabling disclosure for one of ordinary skill in the art to make and use the systems and methods according to the disclosure, it should be under- That which is claimed is:

1. A method for high-speed analysis of samples, comprising:
   illuminating a sample with an illumination light at an inspection point by directing the illumination light through the sample;
   providing a light sensitive detector, the detector producing an output based on a received light;
   directing a light from the sample toward the light sensitive detector through at least one multivariate optical element, the light from the sample carrying information about the sample;
   directing at least a portion of the illumination light toward the light sensitive detector through a reference optical element; and
   analyzing the signals produced by the detector, the analysis being based on a comparison of the signal produced from light passing through the at least one multivariate optical element and the signal produced from the portion of the illumination light passing through the reference optical element,
   wherein the same light sensitive detector is configured to receive the light from the sample and the portion of the illumination light passing through the reference optical element.

2. The method of claim 1, wherein the sample is at least one of a pharmaceutical tablet, a pharmaceutical powder, a food material, a chemical, a liquid, a gas, an emulsion, a solution, or a mixture thereof.

3. The method of claim 1, wherein the sample is a powder mixture in a closed container, the container being at least partially transparent to the illuminating light.

4. The method of claim 1, further comprising:
   moving the sample past the inspection point.

5. The method of claim 1, wherein directing a light from the sample comprises directing light reflected from the sample.

6. The method of claim 1, wherein directing a light from the sample comprises directing a light by way of a diversion path.

7. The method of claim 6, wherein directing a light comprises directing a light using a focusing lens.

8. The method of claim 7, wherein the focusing lens is a focusing mirror.

9. The method of claim 1, wherein directing light comprises directing light using a focusing lens.

10. The method of claim 9, where the focusing lens is a collimating mirror.

11. The method of claim 1, wherein the illumination light comprises a spectral-specific light.

12. The method of claim 11, further comprising:
    illuminating the sample through an optic window, the optic window being configured to focus the spectral-specific light onto a sample at the inspection point.

13. The method of claim 1, wherein the sample comprises a plurality of discrete portions.

14. The method of claim 13, wherein the plurality of discrete portions are disposed in closed containers, the containers at least partially transparent to the spectral-specific light.

15. A method for high-speed analysis of samples, comprising:
    illuminating a sample with light at an inspection point by directing the light through the sample;
    providing a light sensitive detector, the detector producing an output based on received light;
    directing light from the sample toward the light sensitive detector through at least one multivariate optical element, the light from the sample carrying information about the sample;
    directing at least a portion of the sample illuminating light toward the light sensitive detector through a reference optical element; and
    analyzing the signals produced by the detector, the analysis being based on a comparison of the signal produced from light passing through the at least one multivariate optical element and the signal produced from light passing through the reference optical element;
    wherein directing light toward the light sensitive detector comprises directing light through a plurality of multivariate optical elements, and wherein directing a portion of the sample illuminating light comprises directing a portion of the sample illuminating light through a plurality of reference optical elements.

16. The method of claim 15, wherein directing light comprises directing light alternately through differing multivariate optical elements and corresponding reference elements in sequence.

17. The method of claim 15 wherein the sample includes a mixture of oil and water.

18. The method of claim 1 wherein the reference optical element includes an adjustable aperture.

19. The method of claim 1 further comprising combining a portion of the light from the sample and a portion of the light directed through the reference optical element to measure a baseline.

20. The method of claim 1 wherein the sample includes a mixture of oil and water.

21. The method of claim 1 further including a second light sensitive detector configured to receive light from the sample and the portion of the illumination light passing through the reference optical element.

* * * * *